Figure 2:
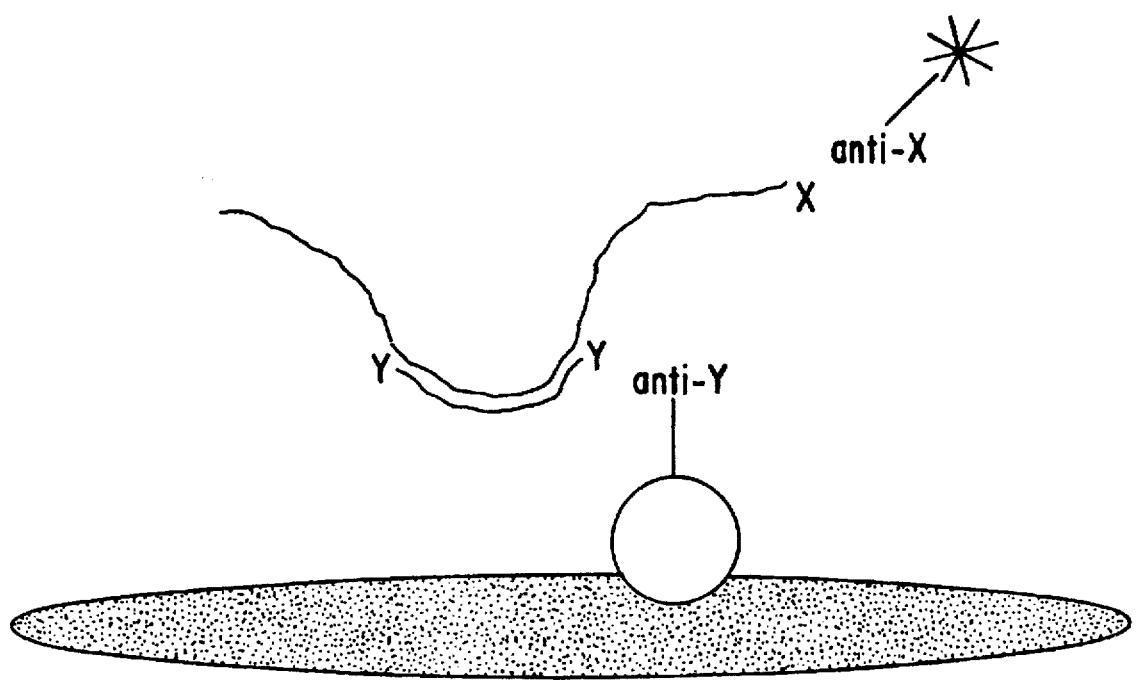

United States Patent [19]
Marshall et al.

[11] Patent Number: 5,709,997
[45] Date of Patent: Jan. 20, 1998

[54] NUCLEIC ACID DETECTION OF HEPATITIS GB VIRUS

[75] Inventors: Ronald L. Marshall, Zion; Cynthia Jou, Libertyville; John N. Simons, Grayslake, all of Ill.; Thomas P. Leary; A. Scott Muerhoff, both of Kenosha, Wis.; Suresh M. Desai, Libertyville; Isa K. Mushahwar, Grayslake, both of Ill.

[73] Assignee: Abbott Laboratories, Abbott Park, Ill.

[21] Appl. No.: 635,309

[22] Filed: Apr. 19, 1996

Related U.S. Application Data

[60] Provisional application No. 60/002,255, Aug. 14, 1995.

[51] Int. Cl.$^6$ .............................. C12Q 1/70; C12Q 1/68; C12P 19/34; C07H 21/04
[52] U.S. Cl. ..................... 435/5; 435/6; 435/91.2; 435/810; 536/24.32; 536/24.33; 935/8; 935/77; 935/78
[58] Field of Search ..................... 435/5, 6, 91.2, 435/810; 935/8, 77, 78; 536/24.32, 24.1, 23.1, 24.33

[56] References Cited

FOREIGN PATENT DOCUMENTS

| | | |
|---|---|---|
| 0318216 | 5/1989 | WIPO . |
| 9000597 | 1/1990 | WIPO . |
| 9408002 | 4/1994 | WIPO . |
| 9418217 | 8/1994 | WIPO . |
| 9532290 | 11/1995 | WIPO . |
| 9532291 | 11/1995 | WIPO . |
| 9532292 | 11/1995 | WIPO . |
| 9506266 | 5/1996 | WIPO . |

OTHER PUBLICATIONS

A. S. Muerhoff et al., *Journal of Virological Methods*, vol. 62, pp. 55–82 (1996).

P. Tijssen, "Practice and Theory of Enzyme Immunoassays", Elsevier, Amsterdam, pp. 333–340 (1985).

S. Vijayasarathy et al., *Nucleic Acids Research*, vol. 18, No. 10, pp. 2967–2975 (1990).

S. K. Kuwada et al., *The American Journal of Gastroenterology*, vol. 89, No. 1, pp. 57–61 (1994).

U.S. Ser. No. 8,389,886, J. Kim et al. filed Jan. 15, 1995.
U.S. Ser. No. 8,357,509, J. Kim et al. filed Dec. 16, 1994.
U.S. Ser. No. 8,344,271, K. Fry et al. filed Nov. 23, 1994.
U.S. Ser. No. 8,329,729 J. Kim et al. filed Oct. 26, 1994.
U.S. Ser. No. 8,285,558, filed J. Kim et al. filed Aug. 3, 1994.
U.S. Ser. No. 8,246,985, J. Kim et al. filed May 20, 1994.

T. Peters et al., *Frequency of Hepatitis C in Acute Post–Transfusion Hepatitis After Open–Heart Surgery: A Prospective Study in 1,476 Patients, Journal of Medical Virology*, vol. 39: 139–145 (1993).

R. Purcell, *The Discovery of the Hepatitis Viruses, Gastroenterology* vol. 104 No. 4: 955–963 (1993).

G. Dawson et al., *Solid–phase enzyme–linked immunosobent assay for hepatitis E virus IgG and IgM antibodies utilizing recombinant antigens and synthetic peptides, Journal of Virological Methods* vol. 38: 175–186 (1992).

P. Yarbough et al., *Hepatitis E Virus: Identification of Type–Common Epitopes, Journal of Virology* vol. 65 No. 11: pp. 5790–5797 (1991).

H. Alter et al., *Detection of Antibody to Hepatitis C Virus in Prospectively Followed Transfusion Recipients with Acute and Chronic Non–A, Non–B Hepatitis, The New England Journal of Medicine* vol. 321 No. 22: pp. 1494–1500 (1989).

(List continued on next page.)

Primary Examiner—W. Gary Jones
Assistant Examiner—Debra Shoemaker
Attorney, Agent, or Firm—Priscilla E. Porembski

[57] ABSTRACT

Nucleic oligomer probes useful for detection of HGBV in test samples. Also provided are assays which utilize these probes and test kits which contain these oligomer probes.

30 Claims, 2 Drawing Sheets

OTHER PUBLICATIONS

M. Alter et al., Risk Factors for Acute Non–A, Non–B Hepatitis in the United States and Association With Hepatitis C Virus Infection, *JAMA* vol. 264 No. 17: pp. 2231–2235 (1990).

J. Dienstag, Hepatitis Non–A, Non–B: C at Last, *Gastroenterology* vol. 99 No. 4: pp. 1177–1180 (1990).

G. Reyes et al., Isolation of a cDNA from the Virus Responsible for Enterically Transmitted Non–A, Non–B Hepatitis, *Science* vol. 247 : pp. 1335–1339 (1990).

G. Kuo et al., An Assay for Circulating Antibodies to a Major Etiologic Virus of Human Non–A, Non–B Hepatitis, *Science* vol. 244 : pp. 362–364 (1989).

A. Weiner et al., Detection of hepatitis C viral sequences in non–A, non–B hepatitis, *The Lancet* vol. 335: pp. 1–3 (1990).

G. Schlauder et al., Viraemia in Egyptian children with hepatitis E virus infection, *The Lancet* vol. 341: p. 378 (1993).

N. Lisitsyn et al., Cloning the Differences Between Two Complex Genomes, *Science* vol. 259: pp. 946–951 (1993).

V. Thiers et al., Post–transfusional anti–HCV–negative non–A non–B hepatitis (II) serological and Polymerase chain reaction analysis for hepatitis C and Hepatitis B viruses, *Journal of Hepatology* vol. 18: pp. 34–39 (1993).

Hepatitis C virus upstanding, *The Lancet* vol. 335: pp. 1431–1432 (1990).

W. Parks et al., Attempted Isolation of Hepatitis Viruses in Marmosets, *The Journal of Infectious Diseases* vol. 120 No. 5: 539–547 (1969).

A. Holmes et al., Specific Neutralization of Human Hepatitis Type A in Marmoset Monkeys, *Nature* vol. 243: pp. 419–420 (1973).

P. Provost et al., Physical, Chemical and Morphologic Dimensions of Human Hepatitis A Virus Strain CR326 (38578), *Proceedings of the Society for Experimental Biology and Medicine* vol. 148: pp. 532–539 (1975).

Q. Choo et al., Isolation of a cDNA Clone Derived from a Blood–Borne Non–A, Non–B Viral Hepatitis Genome, *Science* vol. 244: pp. 359–361 (1989).

J. Almeida et al., Morphology of the GB hepatitis agent, *Nature* vol. 261: pp. 608–609 (1976).

F. Deinhardt et al., Studies on the Transmission of Human Viral Heptitis to Marmoset Monkeys, *Journal of Experimental Medicine* vol. 125: pp. 673–688, Plate 81–86 (1966).

J. Dienstag, Non–A, Non–B Hepatitis. II. Experimental Transmission, Putative Virus Agents and Markers, and Prevention, *Gastroenterology* vol. 85 No. 3: pp. 743–768 (1983).

F. Hollinger et al., Transfusion–Transmitted Viruses Study: Experimental Evidence for Two Non–A, Non–B Hepatitis Agents, *Journal of Infectious Diseases* vol. 142 No. 3: pp. 400–407 (1980).

D. Bradley, Transmission, Etiology, and Pathogenesis of Viral Hepatitis Non–A, Non–B in Non–Human Primates, *Advances in Hepatitis Research*: pp. 268–280 (1984).

F. Deinhardt et al., Hepatitis in marmosets, *The American Journal of the Medical Sciences* vol. 270: pp. 73–80 (1975).

S. Kalter, Comparison of Infectivity of Human Non–A/Non–B Hepatitis and the GB Hepatitis Agent in Marmosets, *Viral and Immunological Diseases in Nonhuman Primates*;: pp. 221–224 (1983).

E. Tabor et al., Transmission of Human Non–A, Non–B Hepatitis to Chimpanzees Following Failure to Transmit GB Agent Hepatitis, *Journal of Medical Virology:* pp. 103–108 (1980).

D. Bradley et al., Posttransfusion Non–A, Non–B Hepatitis: Physicochemical Properties of Two Distinct Agents, *The Journal of Infectious Diseases* vol. 148 No. 2: pp. 254–265 (1983).

J. Dienstag, Virus–like particles and GB agent hepatitis, *Nature* vol. 264: pp. 260–261 (1976).

P. Karayiannis et al., Studies of GB Hepatitis Agent in Tamarins, *Hepatology* vol. 9 No. 2: pp. 186–192 (1989).

J. Melnick, Classification of Hepatitis A Virus as Enterovirus Type 72 and of Hepatitis B Virus as Hepadnavirus Type 1, *Intervirology* vol. 18: pp. 105–106 (1982).

W. Parks et al., Characterization of Marmoset Hepatitis Virus, *The Journal of Infectious Diseases* vol. 120 No. 5: pp. 548–559 (1969).

S. Feinstone et al., Hepatitis A: Detection by Immune Electron Microscopy of a Viruslike Antigen Associated with Acute Illness, *Science* vol. 182: pp. 1026–1028 (1973).

E. Tabor et al., Lack of Susceptibility of Marmosets to Human Non–A, Non–B Hepatitis, *The Journal of Infectious Diseases* vol. 140 No. 5: pp. 794–797 (1979).

E. Fagan et al., Toga Virus–Like Particles in Acute Liver Failure Attributed to Sporadic Non–A, Non–B Hepatitis and Recurrence After Liver Trasplantation, *Journal of Medical Virology* vol. 38: pp. 71–77 (1992).

J. Dienstag, Virus particles in marmoset hepatitis, *Nature* vol. 267: pp. 729–730 (1977).

F. Deinhardt et al., Hepatitis in Marmosets, *The Journal of Infectious Diseases* vol. 121 No. 3: pp. 351–354 (1970).

F. Deinhardt et al., The Mythology of Various Hepatitis A Virus Isolates, *International Symposium on Viral Hepatitis:* pp. 390–404 (1975) vol. 30.

M. Alter et al., The Natural History of Community–Acquired Hepatitis C in the United States, *The New England Journal of Medicine* vol. 327 No. 27: pp. 1899–1905 (1992).

R. Gibbs, Polymerase chain reaction techniques, *Analytical Biotechnology:* pp. 69–75 (1991).

S. Friedman et al., The core element of the EcoRII methylase as defined by protease digestion and deletion analysis, *Nucleic Acids Research* vol. 19 No.19: pp. 5403–5408 (1991).

A. Rosenthal et al., Genomic walking and sequencing by oligo–cassette mediated polymerase chain reaction, *Nucleic Acids Research* vol. 18 No. 10: pp. 3095–3096 (1990).

A. Akowitz, Protected endogenous retroviral sequences copurify with infectivity in experimental Creutzfeldt–Jakob disease, *Archives of Virology* vol. 130: pp. 301–316 (1993).

Non–A, Non–B?, *The Lancet* vol. 2: pp. 64–65 (1975).

F. Hollinger, Non–A, Non–B Hepatitis Viruses, *Virology:* pp. 2239–2273 (1990).

J. Dienstag, Non–A, Non–B Hepatitis I. Recognition, Epidemiology, and Clinical Features, *Gastroenterology* vol. 85 No. 2: pp. 439–462 (1983).

J. Strauss et al., Structure and Function of the Flavivirus and Pestivirus Genomes, *Viral Hepatitis and Liver Disease:* pp. 333–344 (1990).

H. Alter et al., Posttransfusion Hepatitis After Exclusion of Commercial and Hepatitis–B Antigen–Positive Donors, *Annals of Internal Medicine* vol. 77 No. 5: pp. 691–699 (1972).

H. Alter et al., Clinical and Serological Analysis of Transfusion–Associated Hepatitis, *The Lancet*: pp. 838–841 (1975).

S. Feinstone et al., Transfusion–Associated Hepatitis Not Due To Viral Hepatitis Type A or B, *The New England Journal of Medicine* vol. 292 No. 15: pp. 767–770 (1975).

J. Simons et al., Identification of two flavivirus–like genomes in the GB Hepatitis agent, *Proc. Natl. Acad. Sci. USA* vol. 92: pp. 3401–3405 (1995).

J. Simons et al., Isolation of novel virus–like sequences associated with human hepatitis, *Nature Medicine* vol. 1 No. 6: pp. 564–569 (1995).

G. Schlauder et al., Molecular and Serologic Analysis in the Transmission of the GB Hepatitis Agents, *Journal of Medical Virology* vol. 46: pp. 81–90 (1995).

M. Yoshiba et al., Detection of the GBV–C hepatitis virus genome in serum from patients with fulminant hepatitis of unknown aetiology, *The Lancet* vol. 346: pp. 1131–1132 (1995).

J. Linnen et al., Molecular Cloning and Disease Association of Hepatitis G Virus: A Transfusion–Transmissible Agent, *Science* vol. 271: pp. 505–508 (1996).

A. Zuckerman, The new GB hepatitis viruses, *The Lancet* vol. 345: pp. 1453–1455 (1995).

L. Altman, Three Newly Discovered Viruses May Cause Unexplained Hepatitis, *The New York Times Medical Science*, Apr. 11, 1995.

L. Altman, Newly Found Viruses May Cause Hepatitis, *The New York Times Medical Science*, Apr. 10, 1995.

T. Leary et al., Sequence and Genomic Organization of GBV–C: A novel Member of the Flaviviridae Associated With Human Non–A–E Hepetitis, *Journal of Medical Virology* vol. 48: pp. 61–67 (1996).

G. Caetano–Anolles et al., DNA Amplification Fingerprinting Using Arbitrary Oligonucleotide Primers, *Applied Biochemistry and Biotechnology* vol. 42: pp. 189–200 (1993).

B. Bassam, DNA amplification fingerprinting of bacteria, *Applied Microbiology and Biotechnology* vol. 38: pp. 70–76 (1992).

G. Caetano–Anolles et al., DNA Amplification Fingerprinting Using Very Short Arbitrary Oligonucleotide Primers, *Biotechnology* vol. 9: pp. 553–557 (1991).

J. Welsh et al., Fingerprinting genomes using PCR with arbitrary primers, *Nucleic Acids Research* vol. 18 No. 24: pp. 7213–7218 (1990).

J. Welsh et al., Arbitrarily primed PCR fingerprinting of RNA, *Nucleic Acids Research* vol. 20 No. 19: pp. 4965–4970 (1992).

J. Williams et al., DNA polymorphisms amplified by arbitrary primers are useful as genetic markers, *Nucleic Acids Research* vol. 18 No. 22: pp. 6531–6535 (1990).

P. Liang et al., Differential Display of Eukaryotic Messenger RNA by Means of the Polymerase Chain Reaction, *Science* vol. 257: pp. 967–971 (1992).

P. Liang et al., Distribution and cloning of eukaryotic mRNAs by means of differential display: refinements and optimization, *Nucleic Acids Research* vol. 21 No. 14: pp. 3269–3275 (1993).

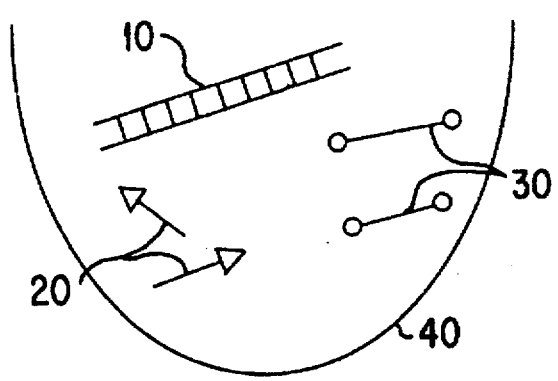
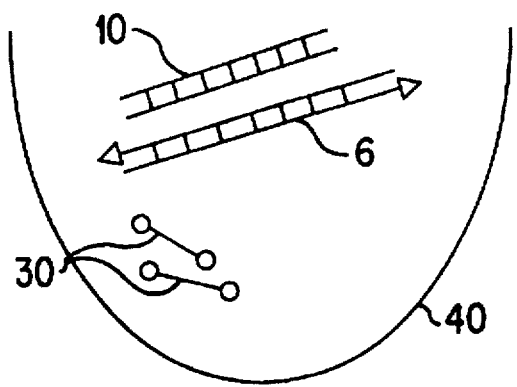
FIG. 1a
FIG. 1b
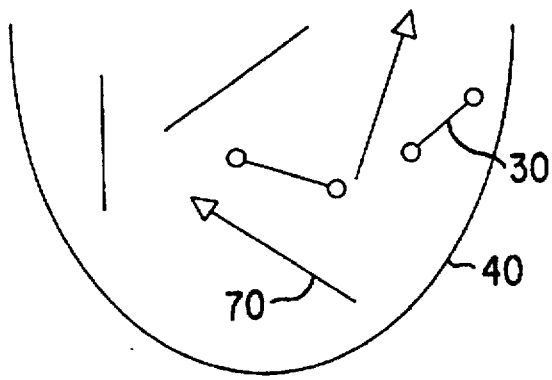
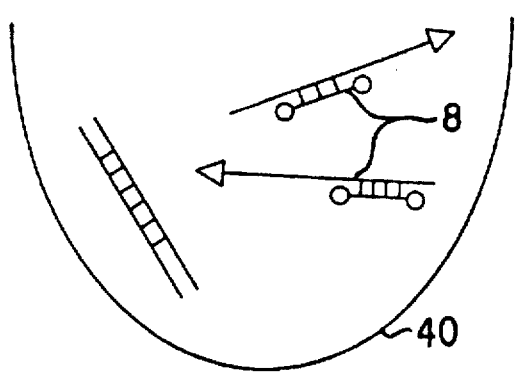
FIG. 1c
FIG. 1d
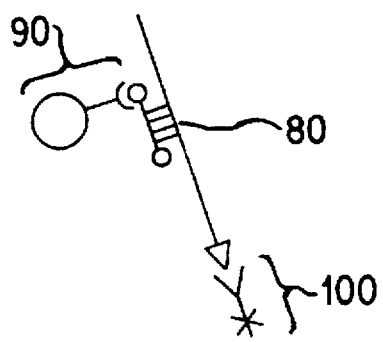
FIG. 1e

NUCLEIC ACID DETECTION OF HEPATITIS GB VIRUS

RELATED APPLICATIONS

This application claims the benefit of U.S. Provisional application Ser. No. 60/002,255 filed Aug. 14, 1995.

This application also is related to patent applications U.S. Ser. No. 08/480,995 filed Jun. 7, 1995, U.S. Ser. No. 08/473,475 filed Jun. 7, 1995 and U.S. Ser. No. 08/417,629, filed Apr. 6, 1995, which are continuation-in-part applications of U.S. Ser. No. 08/424,550 filed Jun. 5, 1995, which is a continuation-in-part application of U.S. Ser. No. 08/377, 557 filed Jan. 30, 1995 now abandoned, which is a continuation-in-part of U.S. Ser. No. 08/344, 185 filed Nov. 23, 1994 now abandoned and U.S. Ser. No. 08/344,190 filed Nov. 23, 1994, which are each continuation-in-part applications of Ser. No. 08/283,314 filed Jul. 29, 1994 now abandoned, which is a continuation-in-part application of U.S. Ser. No. 08/242,654, filed May 13, 1994, which is a continuation-in-part application of U.S. Ser. No. 08/196,030 filed Feb. 14, 1994, all of which enjoy common ownership and each of which is incorporated herein by reference.

BACKGROUND OF THE INVENTION

This invention relates generally to HGBV, and more particularly, relates to nucleic acid probes and primers useful for detection of hepatitis GB virus.

Several lines of epidemiological and laboratory evidence have suggested the existence of more than one parenterally transmitted non-A, non-B (NANB) hepatitis-causing agent, including multiple attacks of acute NANBH in intraveneous drug users, distinct incubation periods of patients acquiring NANBH post-transfusion, the outcome of cross-challenge chimpanzee experiments, the ultrastructural liver pathology of infected chimpanzees and the differential resistance of the putative agents to chloroform. J. L. Dienstag, *Gastroenterology* 85:439–462 (1983); J. L. Dienstag, *Gastroenterology* 85:743–768 (1983); F. B. Hollinger et al., *J. Infect. Dis.* 142:400–407 (1980); D. W. Bradley in F. Chisari, ed., *Advances in Hepatitis Research, Masson*, N.Y., pp. 268–280 (1984); and D. W. Bradley et al., *J. Infect. Dis.* 148:254–265 (1983).

The detection of hepatitis C virus (HCV) antibody in donor samples now eliminates 70 to 80% of NANBH infected blood in the blood supply system. Thus, the detection of HCV has not totally prevented the transmission of hepatitis due to NANB hepatitis agents. H. Alter et al., *New Eng. J. Med.* 321:1494–1500 (1989). Recent publications also have questioned whether additional hepatitis agents may be responsible for post-transfusion hepatitis (PTH) and for community acquired acute and/or chronic hepatitis that is not associated with PTH. For example, of 181 patients monitored in a prospective clinical survey conducted in France from 1988 to 1990, investigators noted a total of 18 cases of PTH. Thirteen of these 18 patients tested negative for anti-HCV antibodies, hepatitis B virus surface antigen (HBsAg), hepatitis B virus (HBV) and HCV nucleic acids. The authors speculated as to the potential importance of a non-A, non-B, non-C agent causing PTH. V. Thiers et al., *J. Hepatology* 18:34–39 (1993). Also, of 1,476 patients monitored in another study conducted in Germany from 1985 to 1988, 22 cases of documented cases of PTH were not related to infection with HBV or HCV. T. Peters et al., *J. Med. Virol.* 39:139–145 (1993).

Recently, a new family of flaviviruses detected in patients with clinically diagnosed hepatitis was reported. This new family of viruses has been named the "GB" viruses, after the initials of the patient first infected with the virus. These viruses have been reported by J. N. Simons et al., *Proc. Natl. Acad. Sci. USA* 92:3401–3405 (1995); and J. N. Simons et al., *Nature Medicine* 1(6):564–569 (1995). Studies currently are underway to determine the clinical and epidemiological significance of these viruses.

The detection of HGBV in test samples can be enhanced by the use of DNA hybridization assays which utilize DNA oligomers as primers and detection probes. Since the amount of DNA target nucleic acid present in a test sample may be in minute amounts, target DNA usually is amplified and then detected. Methods for amplifying and detecting a target nucleic acid sequence that may be present in a test sample are well-known in the art. Such methods include the polymerase chain reaction (PCR) described in U.S. Pat. Nos. 4,683,195 and 4,683,202, the ligase chain reaction (LCR) described in EP-A-320 308, gap LCR (GLCR) described in European Patent Application EP-A-439 182 and U.S. Pat. No. 5,427,930 which is incorporated herein by reference, multiplex LCR described in International Patent Application No. WO 93/20227, and the like. These methods have found widespread application in the medical diagnostic field as well as in the fields of genetics, molecular biology and biochemistry.

It would be advantageous to provide DNA oligomer probes derived from HGBV and diagnostics and test kits which utilize these probes. Such probes could greatly enhance the ability of the medical community to more accurately diagnose acute and/or chronic viral hepatitis and could provide a safer blood and organ supply by detecting non-A, non-B and non-C hepatitis in these blood and organ donations.

SUMMARY OF THE INVENTION

The present invention provides novel hepatitis GB virus (HGBV) DNA oligomer primers and probes. These DNA primers and probes are identified as SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14 and SEQUENCE ID NO 15. Also provided are SEQUENCE ID NO 16, SEQUENCE ID NO 17, SEQUENCE ID NO 18, SEQUENCE ID NO 19, SEQUENCE ID NO 20, SEQUENCE ID NO 21, SEQUENCE ID NO 22, SEQUENCE ID NO 23, SEQUENCE ID NO 24, SEQUENCE ID NO 25, SEQUENCE ID NO 26, SEQUENCE ID NO 27 SEQUENCE ID NO 28, SEQUENCE ID NO 29, SEQUENCE ID NO 30 and SEQUENCE ID NO 31. SEQUENCE ID NOs 1, 2, 3, 4, 5, 16, 17, 18, 19, 20, 21, 22, 23, 24, 25, 26 and 27 are specific for the 5' non-translated region (NTR) of GBV.SEQUENCE ID NOs 6, 7, 8, 9, 10, 11, 12, 13, 14, 15, 28, 29, 30 and 31 are specific for the NS3 region of HGBV. The HGBV primers specific for the 5' NTR region of HGBV are SEQUENCE ID NO 1 and SEQUENCE ID NO 2; SEQUENCE ID NOs 1 and 16; SEQUENCE ID NOs 18 and 19; and SEQUENCE ID NOs 21 and 22. The HGBV primers specific for the NS3 region of HGBV are SEQUENCE ID NO 6 and SEQUENCE ID NO 7; also, SEQUENCE ID NOs 30 and 31.

The present invention also provides an assay for detecting the presence of HGBV in a test sample, which comprises (a) contacting a test sample suspected of containing a target HGBV DNA sequence with a pair of HGBV primers selected from the group consisting of the pair of SEQUENCE ID NO 1 and SEQUENCE ID NO 2, the pair of SEQUENCE ID NO 6 and 7, the pair of SEQUENCE ID NO 1 and SEQUENCE ID NO 16, the pair of SEQUENCE ID NO 18 and SEQUENCE ID NO 19, the pair of SEQUENCE ID NO 21 and SEQUENCE ID NO 22, and the pair of SEQUENCE ID NO 30 and SEQUENCE ID NO 31, and a detection probe specific for HGBV comprising at least one HGBV probe selected from the group consisting of SEQUENCE ID NO 3, SEQUENCE ID NO 4, SEQUENCE ID NO 5, SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 17, SEQUENCE ID NO 20, SEQUENCE ID NO 23, SEQUENCE ID NO 28 and SEQUENCE ID NO 29, and (b) detecting the presence of the target DNA in the test sample. The HGBV probe can be conjugated to a signal generating compound or a hapten. This signal generating compound is selected from the group consisting of a chemiluminescent compound, a fluorescein compound and an enzyme. The hapten is selected from the group consisting of adamantane, carbazole, fluorescein and biotin. The reaction can be performed on a solid phase. The probe and the primer each can be attached to a different hapten such as adamantane and carbazole, and attachment can occur at either the 5' end, the 3' end, both the 5' and 3' ends; or, more than one hapten can be attached at or near the 5' or the 3' end. Also, the reaction can be amplified by the polymerase chain reaction (PCR).

Also provided is a test kit for detecting target HGBV DNA in a test sample, comprising (a) a container containing an HGBV primer, wherein the primer is a pari selected from the group consisting of the pair of SEQUENCE ID NO 1 and SEQUENCE ID NO 2, the pair of SEQUENCE ID NO 6 and 7, the pair of SEQUENCE ID NO 1 and SEQUENCE ID NO 16, the pair of SEQUENCE ID NO 18 and SEQUENCE ID NO 19, the pair of SEQUENCE ID NO 21 and SEQUENCE ID NO 22, and the pair of SEQUENCE ID NO 30 and SEQUENCE ID NO 31; and (b) a container containing a detection probe specific for HGBV selected from the group consisting of SEQUENCE ID NO 3, SEQUENCE ID NO 4, SEQUENCE ID NO 5, SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 17, SEQUENCE ID NO 20, SEQUENCE ID NO 23, SEQUENCE ID NO 28 and SEQUENCE ID NO 29. The HGBV probe can be conjugated to a hapten or a detectable signal generating compound. This signal generating compound is selected from the group consisting of a chemiluminescent compound, a fluorescein compound and an enzyme. The hapten is selected from the group consisting of adamantane, carbazole, fluorescein and biotin. The reaction can be performed on a solid phase. The reaction can be amplified by an amplification process such as PCR. The probe and the primer each can be attached to a different hapten such as adamantane and carbazole, and attachment can occur at either the 5' end, the 3' end, both the 5' and Y ends; or, more than one hapten can be attached at or near the 5' or the 3' end.

BRIEF DESCRIPTION OF THE DRAWINGS

FIG. 1 A–F are diagrams which describe the steps of the preferred assay method of the invention.

FIG. 2 is a diagram of the reaction complex.

DETAILED DESCRIPTION OF THE INVENTION

The present invention provides DNA oligomer probes, methods for determining the presence of the HGBV target nucleotide sequences utilizing these probes and test kits which contain these probes.

Portions of the nucleic acid sequences derived from HGBV are useful as probes to determine the presence of HGBV in test samples, and to isolate naturally occurring variants. These sequences also make available polypeptide sequences of HGBV antigens encoded within the HGBV genome(s) and permit the production of polypeptides which are useful as standards or reagents in diagnostic tests and/or as components of vaccines. Isolation and sequencing of other portions of the HGBV genome also can be accomplished by utilizing probes or PCR primers derived from these nucleic acid sequences, thus allowing additional probes and polypeptides of the HGBV to be established, which will be useful in the diagnosis and/or treatment of HGBV, both as a prophylactic and therapeutic agent. These nucleic acid probes are identified as SEQUENCE ID NO 1, SEQUENCE ID NO 2, SEQUENCE ID NO 3, SEQUENCE ID NO 4, SEQUENCE ID NO 5, SEQUENCE ID NO 6, SEQUENCE ID NO 7, SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 16, SEQUENCE ID NO 17, SEQUENCE ID NO 18, SEQUENCE ID NO 19, SEQUENCE ID NO 20, SEQUENCE ID NO 21, SEQUENCE ID NO 22, SEQUENCE ID NO 23, SEQUENCE ID NO 24, SEQUENCE ID NO 25, SEQUENCE ID NO 26, SEQUENCE ID NO 27, SEQUENCE ID NO 28, SEQUENCE ID NO 29, SEQUENCE ID NO 30 and SEQUENCE ID NO 31.

The present invention provides test kits containing reagents which can be used for the detection of the presence and/or amount of polynucleotides derived from HGBV. These reagents employed for the assay can be provided in the form of a test kit with one or more containers such as vials or bottles, with each container containing a separate reagent such as a nucleic acid probe or a cocktail of nucelic acid probes employed in the assay. Other components such as buffers, controls, and the like, known to those of ordinary skill in art, may be included in such test kits.

The term "Hepatitis GB Virus" or "HGBV", as used herein, collectively denotes a viral species which causes non-A, non-B, non-C, non-D, non-E hepatitis or possibly other diseases in mammals such as man, and attenuated strains or defective interfering particles derived therefrom. This may include acute viral hepatitis transmitted by contaminated foodstuffs, drinking water, and the like; hepatitis due to HGBV transmitted via person to person contact (including sexual transmission, respiratory and parenteral routes) or via intraveneous drug use. The methods as described herein will allow the identification of individuals who have acquired HGBV. Individually, the HGBV isolates are specifically referred to as "HGBV-A", "HGBV-B" and "HGBV-C." As described herein, the HGBV genome is comprised of RNA. Analysis of the nucleotide sequence and deduced amino acid sequence of the HGBV reveals that viruses of this group have a genome organization similar to that of the Flaviridae family. Based primarily, but not exclusively, upon similarities in genome organization, the International Committee on the Taxonomy of Viruses has recommended that this family be composed of three genera:

Flavivirus, Pestivirus, and the hepatitis C group. Similarity searches at the amino acid level reveal that the hepatitis GB virus subclones have some, albeit low, sequence resemblence to hepatitis C virus. It now has been demonstrated that HGBV-C is not a genotype of HCV. See, for example, U.S. Ser. No. 08/417,629, filed Apr. 6, 1995, previously incorporated herein by reference.

The term "similarity" and/or "identity" are used herein to describe the degree of relatedness between two polynucleotides or polypeptide sequences. The techniques for determining amino acid sequence "similarity" and/or "identity" are well-known in the an and include, for example, directly determining the amino acid sequence and comparing it to the seqeunces provided herein; determining the nucleotide sequence of the genomic material of the putative HGBV (usually via a cDNA intermediate), and determining the amino acid sequence encoded therein, and comparing the corresponding regions. In general, by "identity" is meant the exact match-up of either the nucleotide sequence of HGBV and that of another strain(s) or the amino acid sequence of HGBV and that of another strain(s) at the appropriate place on each genome. Also, in general, by "similarity" is meant the exact match-up of amino acid sequence of HGBV and that of another strain(s) at the appropriate place, where the amino acids are identical or possess similar chemical and/or physical properties such as charge or hydrophobicity. The programs available in the Wisconsin Sequence Analysis Package, Version 8 (available from the Genetics Computer Group, Madison, Wis., 53711), for example, the GAP program, are capable of calculating both the identity and similarity between two polynucleotide or two polypeptide sequences. Other programs for calculating identity and similarity between two sequences are known in the art.

Additionally, the following parameters are applicable, either alone or in combination, in identifying a strain of HGBV-A, HGBV-B or HGBV-C. It is expected that the overall nucleotide sequence identity of the genomes between HGBV-A, HGBV-B or HGBV-C and a strain of one of these hepatitis GB viruses will be about 45% or greater, since it is now believed that the HGBV strains may be genetically related, preferably about 60% or greater, and more preferably, about 80% or greater.

Also, it is expected that the overall sequence identity of the genomes between HGBV-A and a strain of HGBV-A at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-B and a strain of HGBV-B at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence. Also, it is expected that the overall sequence identity of the genomes between HGBV-C and a strain of HGBV-C at the amino acid level will be about 35% or greater since it is now believed that the HGBV strains may be genetically related, preferably about 40% or greater, more preferably, about 60% or greater, and even more preferably, about 80% or greater. In addition, there will be corresponding contiguous sequences of at least about 13 nucleotides, which may be provided in combination of more than one contiguous sequence.

A polynucleotide "derived from" a designated sequence, for example, the HGBV cDNA, or from the HGBV genome, refers to a polynucleotide sequence which is comprised of a sequence of approximately at least about 6 nucleotides, is preferably at least about 8 nucleotides, is more preferably at least about 10–12 nucleotides, and even more preferably is at least about 15–20 nucleotides corresponding, i.e., similar to or complementary to, a region of the designated nucleotide sequence. Preferably, the sequence of the region from which the polynucleotide is derived is similar to or complementary to a sequence which is unique to the HGBV genome. Whether or not a sequence is complementary to or similar to a sequence which is unique to an HGBV genome can be determined by techniques known to those skilled in the art. Comparisons to sequences in databanks, for example, can be used as a method to determine the uniqueness of a designated sequence. Regions from which sequences may be derived include but are not limited to regions encoding specific epitopes, as well as non-translated and/or non-transcribed regions.

The derived polynucleotide will not necessarily be derived physically from the nucleotide sequence of HGBV, but may be generated in any manner, including but not limited to chemical synthesis, replication or reverse transcription or transcription, which are based on the information provided by the sequence of bases in the region(s) from which the polynucleotide is derived. In addition, combinations of regions corresponding to that of the designated sequence may be modified in ways known in the art to he consistent with an intended use.

The terms "polynucleotide," "oligomer" and "oligonucleotide" are used interchangeably herein.

The term "polynucleotide" as used herein means a polymeric form of nucleotides of any length, either ribonucleotides or deoxyribonucleotides. This term refers only to the primary structure of the molecule. Thus, the term includes double- and single-stranded DNA, as well as double- and single-stranded RNA. It also includes modifications, either by methylation and/or by capping, and unmodified forms of the polynucleotide.

"HGBV containing a sequence corresponding to a cDNA" means that the HGBV contains a polynucleotide sequence which is similar to or complementary to a sequence in the designated DNA. The degree of similarity or complementarity to the cDNA will be approximately 50% or greater, will preferably be at least about 70% , and even more preferably will be at least about 90% . The sequence which corresponds will be at least about 70 nucleotides, preferably at least about 80 nucleotides, and even more preferably at least about 90 nucleotides in length. The correspondence between the HGBV and the cDNA can be determined by methods known in the art, and include, for example, a direct comparison of the sequenced material with the cDNAs described, or hybridization and digestion with single strand nucleases, followed by size determination of the digested fragments.

"Purified viral polynucleotide" refers to an HGBV genome or fragment thereof which is essentially free, i.e., contains less than about 50% , preferably less than about 70% , and even more preferably, less than about 90% of polypeptides with which the viral polynucleotide is naturally associated. Techniques for purifying viral polynucleotides are well known in the art and include, for example, disruption of the particle with a chaotropic agent, and separation of the polynucleotide(s) and polypeptides by ion-exchange chromatography, affinity chromatography, and sedimentation according to density. Thus, "purified viral polypeptide" means an HGBV polypeptide or fragment thereof which is essentially free, that is, contains less than about 50%, preferably less than about 70%, and even more preferably, less than about 90% of of cellular components with which the viral polypeptide is naturally associated. Methods for purifying are known to the routineer.

"Polypeptide" as used herein indicates a molecular chain of amino acids and does not refer to a specific length of the product. Thus, peptides, oligopeptides, and proteins are included within the definition of polypeptide. This term, however, is not intended to refer to post-expression modifications of the polypeptide, for example, glycosylations, acetylations, phosphorylations and the like.

The term "open reading frame" or "ORF" refers to a region of a polynucleotide sequence which encodes a polypeptide; this region may represent a portion of a coding sequence or a total coding sequence.

A "coding sequence" is a polynucleotide sequence which is transcribed into mRNA and/or translated into a polypeptide when placed under the control of appropriate regulatory sequences. The boundaries of the coding sequence are determined by a translation start codon at the 5'-terminus and a translation stop codon at the 3'-terminus. A coding sequence can include, but is not limited to, mRNA, cDNA, and recombinant polynucleotide sequences.

The term "immunologically identifiable with/as" refers to the presence of epitope(s) and polypeptide(s) which also are present in and are unique to the designated polypeptide(s), usually HGBV proteins. Immunological identity may be determined by antibody binding and/or competition in binding. These techniques are known to the routineer and also are described herein. The uniqueness of an epitope also can be determined by computer searches of known data banks, such as GenBank®, for the polynucleotide sequences which encode the epitope, and by amino acid sequence comparisons with other known proteins.

As used herein, "epitope" means an antigenic determinant of a polypeptide. Conceivably, an epitope can comprise three amino acids in a spatial conformation which is unique to the epitope. Generally, an epitope consists of at least five such amino acids, and more usually, it consists of at least eight to ten amino acids. Methods of examining spatial conformation are known in the art and include, for example, x-ray crystallography and two-dimensional nuclear magnetic resonance.

The term "individual" as used herein refers to vertebrates, particularly members of the mammalian species and includes but is not limited to domestic animals, sports animals, primates and humans; more particularly the term refers to tamarins and humans.

The term "plus strand" (or "+") as used herein denotes a nucleic acid that contains the sequence that encodes the polypeptide. The term "minus strand" (or "−") denotes a nucleic acid that contains a sequence that is complementary to that of the "plus" strand.

"Positive stranded genome" of a virus denotes that the genome, whether RNA or DNA, is single-stranded and encodes a viral polypeptide(s).

The term "test sample" refers to a component of an individual's body which is the source of the analyte (such as, antibodies of interest or antigens of interest). These components are well known in the art. These test samples include biological samples which can be tested by the methods of the present invention described herein and include human and animal body fluids such as whole blood, serum, plasma, cerebrospinal fluid, urine, lymph fluids, and various external secretions of the respiratory, intestinal and genitourinary tracts, tears, saliva, milk, white blood cells, myelomas and the like; biological fluids such as cell culture supernatants; fixed tissue specimens; and fixed cell specimens. "Purified HGBV" refers to a preparation of HGBV which has been isolated from the cellular constituents with which the virus is normally associated, and from other types of viruses which may be present in the infected tissue. The techniques for isolating viruses are known to those skilled in the art and include, for example, centrifugation and affinity chromatography.

"PNA" denotes a "peptide nucleic acid" which may be utilized in a procedure such as an assay described herein to determine the presence of a target. PNAs are neutrally charged moieties which can be directed against RNA targets or DNA. PNA probes used in assays in place of, for example, the DNA probes of the present invention, offer advantages not acheivable when DNA probes are used. These advantages include manufacturability, large scale labeling, reproducibility, stability, insensitivity to changes in ionic strength and resistance to enzymatic degradation which is present in methods utilizing DNA or RNA. These PNAs can be labeled with such signal generating compounds as flouorescein, radionucleotides, chemiluminescent compounds, and the like. PNAs or other nucleic acid analogues such as morpholino compounds thus can be used in assay methods in place of DNA or RNA. Although assays are described herein utilizing DNA probes, it is within the scope of the routineer that PNAs or morpholino compounds can be substituted for RNA or DNA with appropriate changes if and as needed in assay reagents.

"Solid phases" ("solid supports") are known to those in the art and include the walls of wells of a reaction tray, test tubes, polystyrene beads, magnetic beads, nitrocellulose strips, membranes, microparticles such as latex particles, sheep (or other animal) red blood cells, duracytes and others. The "solid phase" is not critical and can be selected by one skilled in the art. Thus, latex particles, microparticles, magnetic or non-magnetic beads, membranes, plastic tubes, walls of microliter wells, glass or silicon chips, sheep (or other suitable animal's) red blood cells and duracytes are all suitable examples. Suitable methods for immobilizing probes on solid phases include ionic, hydrophobic, covalent interactions and the like. A "solid phase", as used herein, refers to any material which is insoluble, or can be made insoluble by a subsequent reaction. The solid phase can be chosen for its intrinsic ability to attract and immobilize the capture reagent. Alternatively, the solid phase can retain an additional receptor which has the ability to attract and immobilize the capture reagent. The additional receptor can include a charged substance that is oppositely charged with respect to the capture reagent itself or to a charged substance conjugated to the capture reagent. As yet another alternative, the receptor molecule can be any specific binding member which is immobilized upon (attached to) the solid phase and which has the ability to immobilize the capture reagent through a specific binding reaction. The receptor molecule enables the indirect binding of the capture reagent to a solid phase material before the performance of the assay or during the performance of the assay. The solid phase thus can be a plastic, derivatized plastic, magnetic or non-magnetic metal, glass or silicon surface of a test tube, microtiter well, sheet, bead, microparticle, chip, sheep (or other suitable animal's)

red blood cells, duracytes and other configurations known to those of ordinary skill in the art.

It is contemplated and within the scope of the invention that the solid phase also can comprise any suitable porous material with sufficient porosity to allow access by detection antibodies and a suitable surface affinity to bind antigens. Microporous structures are generally preferred, but materials with gel structure in the hydrated state may be used as well. Such useful solid supports include but are not limited to natural polymeric carbohydrates and their synthetically modified, cross-linked or substituted derivatives, such as agar, agarose, cross-linked alginic acid, substituted and cross-linked guar gums, cellulose esters, especially with nitric acid and carboxylic acids, mixed cellulose esters, and cellulose ethers; natural polymers containing nitrogen; synthetic polymers which may be prepared with suitably porous structures, such as vinyl polymers; porous inorganic materials such as sulfates or carbonates of alkaline earth metals and magnesium, including barium sulfate, calcium sulfate, calcium carbonate, silicates of alkali and alkaline earth metals, aluminum and magnesium; and aluminum or silicon oxides or hydrates, such as clays, alumina, talc, kaolin, zeolite, silica gel, or glass (these materials may be used as filters with the above polymeric materials); and mixtures or copolymers of the above classes, such as graft copolymers obtained by initializing polymerization of synthetic polymers on a pre-existing natural polymer. All of these materials may be used in suitable shapes, such as films, sheets, or plates, or they may be coated onto or bonded or laminated to appropriate inert carriers, such as paper, glass, plastic films, or fabrics.

The porous structure of nitrocellulose has excellent absorption and adsorption qualities for a wide variety of reagents. Nylon also possesses similar characteristics and also is suitable. It is contemplated that such porous solid supports described hereinabove are preferably in the form of sheets of thickness from about 0.01 to 0.5 mm, preferably about 0.1 mm. The pore size may vary within wide limits, and is preferably from about 0.025 to 15 microns, especially from about 0.15 to 15 microns. The surfaces of such supports may be activated by chemical processes which cause covalent linkage of the antigen or antibody to the support. The irreversible binding of the antigen or antibody is obtained, however, in general, by adsorption on the porous material by poorly understood hydrophobic forces. Suitable solid supports also are described in U.S. patent application Ser. No. 07/227,272 now U.S. Pat. No. 5,075,077.

The "indicator reagent" comprises a "signal generating compound" (also termed a "label") which is capable of generating and generates a measurable signal detectable by external means conjugated (attached) to a specific binding member for HGBV. "Specific binding member" as used herein means a member of a specific binding pair. That is, two different molecules where one of the molecules through chemical or physical means specifically binds to the second molecule. In addition to being an antibody member of a specific binding pair for HGBV, the indicator reagent also can be a member of any specific binding pair, including either hapten-anti-hapten systems such as biotin or anti-biotin, avidin or biotin, a carbohydrate or a lectin, a complementary nucleotide sequence, an inhibitor or a receptor molecule, an enzyme cofactor and an enzyme, an enzyme inhibitor or an enzyme, and the like. Furthermore, specific binding pairs can include members that are analogs of the original specific binding members, for example, an analyte-analog. An immunoreactive specific binding member can be an antibody or fragment thereof, an antigen or fragment thereof, or an antibody/antigen complex including those formed by recombinant DNA molecules that is capable of binding either to HGBV as in a sandwich assay, to the capture reagent as in a competitive assay, or to the ancillary specific binding member as in an indirect assay.

The various "signal generating compounds" (labels) contemplated include chromogens, catalysts such as enzymes, luminescent compounds such as fluorescein and rhodamine, chemiluminescent compounds such as dioxetanes, acridiniums, phenanthridiniums and luminol, radioactive elements, and direct visual labels. Examples of enzymes include alkaline phosphatase, horseradish peroxidase, beta-galactosidase, and the like. The selection of a particular label is not critical, but it will be capable of producing a signal either by itself or in conjunction with one or more additional substances.

The term "detection label" refers to a molecule or moiety having a property or characteristic which is capable of detection. A detection label can be directly detectable, as with, for example, radioisotopes, fluorophores, chemiluminophores, enzymes, colloidal particles, fluorescent microparticles and the like; or a label may be indirectly detectable, as with, for example, specific binding members. It will be understood that direct labels may require additional components such as, for example, substrates, triggering reagents, light, and the like to enable detection of the label. When indirect labels are used for detection, they are typically used in combination with a conjugate. A "conjugate" is typically a specific binding member which has been attached or coupled to a directly detectable label. Similarly to the synthesis of solid phase reagents, coupling chemistries for synthesizing a conjugate are well known in the art and can include, for example, any chemical means and/or physical means that does not destroy the specific binding property of the specific binding member or the detectable property of the label.

The term "hapten", as used herein, refers to a partial antigen or non-protein binding member which is capable of binding to an antibody, but which is not capable of eliciting antibody formation unless coupled to a carrier protein. Examples of haptens include biotin, avidin, adamantane, fluorescein and carbazole.

"Analyte," as used herein, is the substance to be detected which may be present in the test sample. The analyte can be any substance for which there exists a naturally occurring specific binding member (such as, an antibody), or for which a specific binding member can be prepared. Thus, an analyte is a substance that can bind to one or more specific binding members in an assay. "Analyte" also includes any antigenic substances such as target nucleotide sequences, haptens, antibodies, and combinations thereof. As a member of a specific binding pair, the analyte can be detected by means of naturally occurring specific binding partners (pairs) such as the use of intrinsic factor protein as a member of a specific binding pair for the determination of Vitamin B 12, the use of folate-binding protein to determine folic acid, or the use of a lectin as a member of a specific binding pair for the determination of a carbohydrate. The analyte can include a protein, a peptide, an amino acid, a nucleotide target, and the like.

Embodiments which utilize ion capture procedures for immobilizing an immobilizable reaction complex with a negatively charged polymer, described in co-pending U.S. patent application Ser. No. 07/150,278 now abandoned corresponding to EP publication 0326100 and U.S. patent application Ser. No. 07/375,029 now abandoned (EP publication no. 0406473), can be employed according to the present invention to effect a fast solution-phase immunochemical reaction. An immobilizable immune complex is separated from the rest of the reaction mixture by ionic interactions between the negatively charged poly-anion/ immune complex and the previously treated, positively charged porous matrix and detected by using various signal generating systems previously described, including those described in chemiluminescent signal measurements as described in co-pending U.S. patent application Ser. No. 06/921,979 now abandoned corresponding to EPO Publication No. 0 273, 115.

Also, the methods of the present invention can be adapted for use in systems which utilize microparticle technology including in automated and semi-automated systems wherein the solid phase comprises a microparticle (magnetic or non-magnetic). Such systems include those described in pending U.S. patent applications Ser. No. 07/425,65 now U.S. Pat. No. 5,244,630 and Ser. No. 07/425,643, now U.S. Pat. No. 5,089,424 which correspond to published EPO applications Nos. EP 0 425 633 and EP 0 424 634, respectively.

The use of scanning probe microscopy (SPM) for analyte detection also is adaptable. In scanning probe microscopy, in particular in atomic force microscopy, the capture phase is adhered to a solid phase and a scanning probe microscope is utilized to detect antigen/antibody complexes which may be present on the surface of the solid phase. The use of scanning tunnelling microscopy eliminates the need for labels which normally must be utilized in many immunoassay systems to detect antigen/antibody complexes. Such a system is described in pending U.S. patent application Ser. No. 07/662,147 now abandoned.

It is contemplated and within the scope of the present invention that the HGBV group of viruses may be detectable in assays by use of a synthetic, recombinant or native probe that is common to all HGBV viruses (termed a "universal" probe). It also is within the scope of the present invention that different synthetic, recombinant or native probes identifying different epitopes from HGBV-A, HGBV-B, HGBV-C, or yet other HGBV viruses, can be used in assay formats. In the later case, these can be coated onto one solid phase, or each separate probe may be coated on separate solid phases, such as microparticles, and then combined to form a mixture of probes which can be later used in assays. Such variations of assay formats are known to those of ordinary skill in the art and are discussed hereinbelow.

The reagents and methods of the present invention are made possible by the provision of a family of closely related nucleotide sequences present in the plasma, serum or liver homogenate of an HGBV infected individual, either tamarin or human. This family of nucleotide sequences is not of human or tamarin origin, since it hybridizes to neither human nor tamarin genomic DNA from uninfected individuals, since nucleotides of this family of sequences are present only in liver (or liver homogenates), plasma or serum of individuals infected with HGBV, and since the sequence is not present in GenBank®. In addition, the family of sequences will show no significant identity at the nucleic acid level to sequences contained within the HAV, HBV, HCV, HDV and HEV genome, and low level identity, considered not significant, as translation products. Infectious sera, plasma or liver homogenates from HGBV infected humans contain these polynucleotide sequences, whereas sera, plasma or liver homogenates from non-infected humans do not contain these sequences. Northern blot analysis of infected liver with some of these polynucleotide sequences demonstrate that they are derived from a large RNA transcript similar in size to a viral genome. Sera, plasma or liver homogenates from HGBV-infected humans contain antibodies which bind to this polypeptide, whereas sera, plasma or liver homogenates from non-infected humans do not contain antibodies to this polypeptide; these antibodies are induced in individuals following acute non-A, non-B, non-C, non-D and non-E hepatitis infection. By these criteria, it is believed that the sequence is a viral sequence, wherein the virus causes or is associated with non-A, non-B, non-C, non-D and non-E hepatitis.

The availability of this family of nucleic acid sequences permits the construction of DNA probes and polypeptides useful in diagnosing non-A, non-B, non-C, non-D, non-E hepatitis due to HGBV infections, and in screening blood donors, donated blood, blood products and individuals for infection. For example, from the sequence it is possible to synthesize DNA oligomers of about eight to ten nucleotides, or larger, which are useful as hybridization probes or PCR primers to detect the presence of the viral genome in, for example, sera of subjects suspected of harboring the virus, or for screening donated blood for the presence of the virus. The family of nucleic acid sequences also allows the design and production of HGBV specific polypeptides which are useful as diagnostic reagents for the presence of antibodies raised during infection with HGBV. Antibodies to purified polypeptides derived from the nucleic acid sequences may also be used to detect viral antigens in infected individuals and in blood. These nucleic acid sequences also enable the design and production of polypeptides which may be used as vaccines against HGBV, and also for the production of antibodies, which then may be used for protection of the disease, and/or for therapy of HGBV infected individuals.

Using determined portions of the isolated HGBV nucleic acid sequences as a basis, oligomers of approximately eight nucleotides or more can be prepared, either by excision or synthetically, which hybridize with the HGBV genome and are useful in identification of the viral agent(s), further characterization of the viral genome, as well as in detection of the virus(es) in diseased individuals. The natural or derived probes for HGBV polynucleotides are a length which allows the detection of unique viral sequences by hybridization. While six to eight nucleotides may be a workable length, sequences of ten to twelve nucleotides are preferred, and those of about 20 nucleotides may be most preferred. These sequences preferably will derive from regions which lack heterogeneity. These probes can be prepared using routine, standard methods including automated oligonucleotide synthetic methods. A complement of any unique portion of the HGBV genome will be satisfactory. Complete complementarity is desirable for use as probes, although it may be unnecessary as the length of the fragment is increased.

When used as diagnostic reagents, the test sample to be analyzed, such as blood or serum, may be treated such as to extract the nucleic acids contained therein. The resulting nucleic acid from the sample may be subjected to gel electrophoresis or other size separation techniques; or, the nucleic acid sample may be dot-blotter without size separation. The probes then are labelled. Suitable labels and methods for attaching labels to probes are known in the art, and include but are not limited to radioactive labels incorporated by nick translation or kinasing, biotin, fluorescent and chemiluminescent probes. Examples of many of these labels are disclosed herein. The nucleic acids extracted from the sample then are treated with the labelled probe under hybridization conditions of suitable stringencies.

The probes can be made completely complementary to the HGBV genome. Therefore, usually high stringency conditions are desirable in order to prevent false positives. However, conditions of high stringency should be used only if the probes are complementary to regions of the HGBV genome which lack heterogeneity. The stringency of hybridization is determined by a number of factors during the washing procedure, including temperature, ionic strength, length of time and concentration of formamide. See, for example, J. Sambrook (supra). Hybridization can be carried out by a number of various techniques. Amplification can be performed, for example, by Ligase Chain Reaction (LCR), Polymerase Chain Reaction (PCR), Q-beta replicase, NASBA, etc.

It is contemplated that the HGBV genome sequences may be present in serum of infected individuals at relatively low levels, for example, approximately $10^2$–$10^3$ sequences per ml. This level may require that amplification techniques be used in hybridization assays, such as the LCR or the PCR. Such techniques are known in the art. For example, the "Bio-Bridge" system uses terminal deoxynucleotide transferase to add unmodified 3'-poly-dT-tails to a nucleic acid probe (Enzo Biochem. Corp.). The poly dt-tailed probe is hybridized to the target nucleotide sequence, and then to a biotin-modified poly-A. Also, in EP 124221 there is described a DNA hybridization assay wherein the analyte is annealed to a single-stranded DNA probe that is complementary to an enzyme-labelled oligonucleotide, and the resulting tailed duplex is hybridized to an enzyme-labelled oligonucleotide. EP 204510 describes a DNA hybridization assay in which analyte DNA is contacted with a probe that has a tail, such as a poly-dT-tail, an amplifier strand that has a sequence that hybridizes to the tail of the probe, such as a poly-A sequence, and which is capable of binding a plurality of labelled strands. The technique first may involve amplification of the target HGBV sequences in sera to approximately $10^6$ sequences/ml. This may be accomplished by following the methods described by Saiki et al., *Nature* 324:163 (1986). The amplified sequence(s) then may be detected using a hybridization assay such as those known in the art. The probes can be packaged in diagnostic kits which include the probe nucleic acid sequence which sequence may be labelled; alternatively, the probe may be unlabelled and the ingredients for labelling could be included with the kit. The kit also may contain other suitably packaged reagents and materials needed or desirable for the particular hybridization protocol, for example, standards as well as instructions for performing the assay.

Other known amplification methods which can be utilized herein include but are not limited to the so-called "NASBA" or "3SR" technique taught in *PNAS USA* 87:1874–1878 (1990) and also discussed in *Nature:* 350 (No. 6313):91–92 (1991) and Q-beta replicase.

Flourescence in situ hybridization ("FISH") also can be performed utilizing the reagents described herein. In situ hybridization involves taking morphologically intact tissues, cells or chromosomes through the nucleic acid hybridization process to demonstrate the presence of a particular piece of genetic information and its specific location within individual cells. Since it does not require homogenization of cells and extraction of the target sequence, it provides precise localization and distribution of a sequence in cell populations. In situ hybridization can identify the sequence of interest concentrated in the cells containing it. It also can identify the type and fraction of the cells in a heterogeneous cell population containing the sequence of interest. DNA and RNA can be detected with the same assay reagents.

PNAs or morpholino compounds can be utilized in FISH methods to detect targets without the need for amplification. If increased signal is desired, mutiple fluorophores can be used to increase signal and thus, sensitivity of the method. Various methods of FISH are known, including a one-step method using multiple oligonucleotides or the conventional multi-step method. It is within the scope of the present invention that these types of methods can be automated by various means including flow cytometry and image analysis.

Assays as described herein may utilize one viral antigen derived from any clone-containing HGBV nucleic acid sequence, or from the composite nucleic acid sequences derived from the HGBV nucleic acid sequences in these clones, or from the HGBV genome from which the nucleic acid sequences in these clones are derived. Or, the immunoassay may use a combination of viral antigens derived from these sources. It also may use, for example, a monoclonal antibody directed against the same viral antigen, or polyclonal antibodies directed against different viral antigens. Assays can include but are not limited to those based on competition, direct reaction or sandwich-type assays. Assays may use solid phases or may be performed by immunoprecipitation or any other methods which do not utilize solid phases. Examples of assays which utilize labels as the signal generating compound and those labels are described herein. Signals also may be amplified by using biotin and avidin, enzyme labels or biotin anti-biotin systems, such as that described in pending U.S. patent application Ser. Nos. 608,849; 070,647; 418,981; and 687,785.

The HGBV nucleic acid sequences may be used to gain further information on the sequence of the HGBV genome, and for identification and isolation of the HGBV agent. Thus, it is contemplated that this knowledge will aid in the characterization of HGBV including the nature of the HGBV genome, the structure of the vital particle, and the nature of the antigens of which it is composed. This information, in turn, can lead to additional polynucleotide probes, polypeptides derived from the HGBV genome, and antibodies directed against HGBV epitopes which would be useful for the diagnosis and/or treatment of HGBV caused non-A, non-B, non-C, non-D and non-E hepatitis.

Synthetic oligonucleotides may be prepared using an automated oligonucleotide synthesizer such as that described by Warner, DNA 3:401 (1984). If desired, the synthetic strands may be labelled with $^{32}$p by treatment with polynucleotide kinase in the presence of $^{32}$P-ATP, using standard conditions for the reaction. DNA sequences including those isolated from genomic or cDNA libraries, may be modified by known methods which include site directed mutagenesis as described by Zoller, *Nucleic Acids Res.* 10:6487 (1982). Briefly, the DNA to be modified is packaged into phage as a single stranded sequence, and converted to a double stranded DNA with DNA polymerase using, as a primer, a synthetic oligonucleotide complementary to the portion of the DNA to be modified, and having the desired modification included in its own sequence. Culture of the transformed bacteria, which contain replications of each strand of the phage, are plated in agar to obtain plaques. Theoretically, 50% of the new plaques contain phage having the mutated sequence, and the remaining 50% have the original sequence. Replicates of the plaques are hybridized to labelled synthetic probe at temperatures and conditions suitable for hybridization with the correct strand, but not with the unmodified sequence. The sequences which have been identified by hybridization are recovered and cloned.

Polymerase chain reaction (PCR) and ligase chain reaction (LCR) are techniques for amplifying any desired nucleic acid sequence (target) contained in a nucleic acid or mixture thereof. In PCR, a pair of primers are employed in excess to hybridize at the outside ends of complementary strands of the target nucleic acid. The primers are each extended by a polymerase using the target nucleic acid as a template. The extension products become target sequences themselves, following dissociation from the original target strand. New primers are then hybridized and extended by a polymerase, and the cycle is repeated to geometrically increase the number of target sequence molecules. PCR is disclosed in U.S. Pat. Nos. 4,683,195 and 4,683,202.

LCR is an alternate mechanism for target amplification. In LCR, two sense (first and second) probes and two antisense (third and fourth) probes are employed in excess over the target. The first probe hybridizes to a first segment of the target strand and the second probe hybridizes to a second segment of the target strand, the first and second segments being positioned so that the primary probes can be ligated into a fused product. Further, a third (secondary) probe can hybridize to a portion of the first probe and a fourth (secondary) probe can hybridize to a portion of the second probe in a similar ligatable fashion. If the target is initially double stranded, the secondary probes will also hybridize to the target complement in the first instance. Once the fused strand of sense and antisense probes are separated from the target strand, it will hybridize with the third and fourth probes which can be ligated to form a complementary, secondary fused product. The fused products are functionally equivalent to either the target or its complement. By repeated cycles of hybridization and ligation, amplification of the target sequence is achieved. This technique is described in EP-A-320,308, hereby incorporated by reference. Other aspects of LCR technique are disclosed in EP-A-439, 182, which is incorporated herein by reference.

In one embodiment, the present invention generally comprises the steps of contacting a test sample suspected of containing a target HGBV nucleotide sequence with amplification reaction reagents comprising a pair of amplification primers, and a detection probe that can hybridize with an internal region of the amplicon sequences. Probes and primers employed according to the method herein provided are labeled with capture and detection labels wherein probes are labeled with one type of label and primers are labeled with the other type of label. Additionally, the primers and probes are selected such that the probe sequence has a lower melt temperature than the primer sequences. The amplification reagents, detection reagents and test sample are placed under amplification conditions whereby, in the presence of target sequence, copies of the target sequence (an amplicon) are produced. In the usual case, the amplicon is double stranded because primers are provided to amplify a target sequence and its complementary strand. The double stranded amplicon is then thermally denatured to produce single stranded amplicon members. Upon formation of the single stranded amplicon members, the mixture is cooled to allow the formation of complexes between the probes and single stranded amplicon members.

Surprisingly, as the single stranded amplicon sequences and probe sequences were cooled, the probe sequences preferentially bound the single stranded amplicon members. Accordingly, the melt temperature of the amplicon produced by the primers should also have a higher melt temperature than the probes. Thus, as the mixture was cooled, the re-formation of the double stranded amplicon would be expected. As previously stated, however, this is not the case. The probes were found to preferentially bind the single stranded amplicon members. Moreover, this preference of probe/single stranded amplicon binding exists even when the primer sequences are added in excess of the probes.

After the probe/single stranded amplicon member hybrids are formed, they are detected. Standard heterogeneous assay formats are suitable for detecting the hybrids using the detection labels and capture labels present on the primers and probes. The hybrids can be bound to a solid phase reagent by virtue of the capture label and detected by virtue of the detection label. In cases where the detection label is directly detectable, the presence of the hybrids on the solid phase can be detected by causing the label to produce a detectable signal, if necessary, and detecting the signal. In cases where the label is not indirectly detectable, the captured hybrids can be contacted with a conjugate, which generally comprises a binding member attached to a directly detectable label. The conjugate becomes bound to the complexes and the conjugates presence on the complexes can be detected with the directly detectable label. Thus, the presence of the hybrids on the solid phase reagent can be determined. Those skilled in the art will recognize that wash steps may be employed to wash away unhybridized amplicon or probe as well as unbound conjugate.

A test sample is typically anything suspected of containing a test sequence. Test samples can be prepared using methodologies well known in the art such as by obtaining a specimen from an individual and, if necessary, disrupting any cells contained therein to release target nucleic acids. Although the target sequence is described as single strandedit also is contemplated to include the case where the target sequence is actually double stranded but is merely separated from its complement prior to hybridization with the amplification primer sequences. In the case where PCR is employed in the preferred method, the ends of the target sequences are usually known. In cases where LCR or a modification thereof is employed in the preferred method, the entire target sequence is usually known. Typically, the target sequence is a nucleic acid sequence such as for example RNA or DNA.

The method provided herein can be used in well known amplification reactions that thermal cycle reaction mixtures, particularly in PCR and GLCR. Amplification reactions typically employ primers to repeatedly generate copies of a target nucleic acid sequence, which target sequence is usually a small region of a much larger nucleic acid sequence. Primers are themselves nucleic acid sequences that are complementary to regions of a target sequence. Under amplification conditions, these primers hybridize or bind to the complementary regions of the target sequence. Copies of the target sequence typically are generated by the process of primer extension and/or ligation which utilizes enzymes with polymerase or ligase activity, separately or in combination, to add nucleotides to the hybridized primers and/or ligate adjacent probe pairs. The nucleotides that are added to the primers or probes, as monomers or preformed oligomers, are also complementary to the target sequence. Once the primers or probes have been sufficiently extended and/or ligated they are separated from the target sequence, for example, by heating the reaction mixture to a "melt temperature" which is one where complementary nucleic acid strands dissociate. Thus, a sequence complementary to the target sequence is formed.

A new amplification cycle then can take place to further amplify the number of target sequences by separating any double stranded sequences, allowing primers or probes to hybridize to their respective targets, extending and/or ligating the hybridized primers or probes and re-separating. The complementary sequences that are generated by amplification cycles can serve as templates for primer extension or filing the gap of two probes to further amplify the number of target sequences. Typically, a reaction mixture is cycled between 20 and 100 times, more typically, a reaction mixture is cycled between 25 and 50 times. The numbers of cycles can be determined by the routineer. In this manner, multiple copies of the target sequence and its complementary sequence are produced. Thus, primers initiate amplification of the target sequence when it is present under amplification conditions.

Generally, two primers which are complementary to a portion of a target strand and its complement are employed in PCR. For LCR, four probes, two of which are complementary to a target sequence and two of which are similarly complementary to the targets complement, are generally employed. In addition to the primer sets and enzymes previously mentioned, a nucleic acid amplification reaction mixture may also comprise other reagents which are well known and include but are not limited to: enzyme cofactors such as manganese; magnesium; salts; nicotinamide adenine dinucleotide (NAD); and deoxynucleotide triphosphates (dNTPs) such as for example deoxyadenine triphosphate, deoxyguanine triphosphate, deoxycytosine triphosphate and deoxythymine triphosphate.

While the amplification primers initiate amplification of the target sequence, the detection (or hybridization) probe is not involved in amplification. Detection probes are generally nucleic acid sequences or uncharged nucleic acid analogs such as, for example peptide nucleic acids which are disclosed in International Patent Application WO 92/20702; morpholino analogs which are described in U.S. Pat. No. 5,185,444, 5,034,506, and 5,142,047; and the like. Depending upon the type of label carried by the probe, the probe is employed to capture or detect the amplicon generated by the amplification reaction. The probe is not involved in amplification of the target sequence and therefore may have to be rendered "non-extendable" in that additional dNTPs cannot be added to the probe. In and of themselves analogs usually are non-extendable and nucleic acid probes can be rendered non-extendable by modifying the 3' end of the probe such that the hydroxyl group is no longer capable of participating in elongation. For example, the 3' end of the probe can be functionalized with the capture or detection label to thereby consume or otherwise block the hydroxyl group. Alternatively, the 3' hydroxyl group simply can be cleaved, replaced or modified. U.S. Patent application Ser. No. 07/049,061 filed Apr. 19, 1993 now U.S. Pat. No. 4,869,905 describes modifications which can be used render a probe non-extendable.

Accordingly, the ratio of primers to probes is not important. Thus, either the probes or primers can be added to the reaction mixture in excess whereby the concentration of one would be greater than the concentration of the other. Alternatively, primers and probes can be employed at in equivalent concentrations. Preferably, however, the primers are added to the reaction mixture in excess of the probes. Thus, primer to probe ratios of, for example, 5:1 and 20:1 are preferred.

While the length of the primers and probes can vary, the probe sequences are selected such that they have a lower melt temperature than the primer sequences. Hence, the primer sequences are generally longer than the probe sequences. Typically, the primer sequences are in the range of between 20 and 50 nucleotides long, more typically in the range of between 20 and 30 nucleotides long. The typical probe is in the range of between 10 and 25 nucleotides long.

Various methods for synthesizing primers and probes are well known in the art. Similarly, methods for attaching labels to primers or probes are also well known in the art. For example, it is a matter of routine to synthesize desired nucleic acid primers or probes using conventional nucleotide phosphoramidite chemistry and instrumetns available from Applied Biosystems, Inc., (Foster City, Calif.), Dupont (Wilmington, Del.), or Milligen (Bedford Mass.). Many methods have been described for labelling oligonucleotides such as the primers or probes of the present invention. Enzo Biochemical (New York, N.Y.) and Clontech (Palo Alto, Calif.) both have described and commercialized probe labeling techniques. For example, a primary amine can be attached to a 3' oligo terminus using 3'-Amine-ON CPG™ (Clontech, Palo Alto, Calif.). Similarly, a primary amine can be attached to a 5' oligo terminus using Aminomodifier II® (Clontech). The amines can be reacted to various haptens using conventional activation and linking chemistries. In addition, copending applications U.S. Ser. Nos. 625,566, filed Dec. 11, 1990 now abandoned and Ser. No. 630,908, filed Dec. 20, 1990, now U.S. Pat. No. 5,290,925 which are each incorporated herein by reference, teach methods for labeling probes at their 5' and 3' termini, respectively. Publications WO92/10505, published 25 Jun. 1992 and WO 92/11388 published 9 Jul. 1992 teach methods for labeling probes at their 5' and 3' ends respectively. According to one known method for labeling an oligonucleotide, a label-phosphoramidite reagent is prepared and used to add the label to the oligonucleotide during its synthesis. See, for example, N.T. Thuong et al., Tet. Letters 29(46):590514 5908 (1988); or J. S. Cohen et al., published U.S. patent application Ser. No. 07/246,688 now abandoned (NTIS ORDER No. PAT-APPL-7-246,688) (1989). Preferably, probes are labeled at their 3' and 5' ends.

Capture labels are carried by the primers or probes and can be a specific binding member which forms a binding pair with the solid phase reagent's specific binding member. It will be understood, of course that the primer or probe itself may serve as the capture label. For example, in the case where a solid phase reagent's binding member is a nucleic acid sequence, it may be selected such that it binds a complementary portion of the primer or probe to thereby immobilize the primer or probe to the solid phase. In cases where the probe itself serves as the binding member, those skilled in the art will recognize that the probe will contain a sequence or "tail" that is not complementary to the single stranded amplicon members. In the case where the primer itself serves as the capture label, at least a portion of the primer will be free to hybridize with a nucleic acid on a solid phase because the probe is selected such that it is not fully complementary to the primer sequence.

Generally, probe/single stranded amplicon member complexes can be detected using techniques commonly employed to perform heterogeneous immunoassays. Preferably, in this embodiment, detection is performed according to the protocols used by the commercially available Abbott LCx® instrumentation (Abbott Laboratories; Abbott Park, Ill.).

FIG. 1 (a)–FIG. 1 (f) provides a diagram of an assay format of the invention. As shown in FIG. 1(a), a test sample containing target sequence 10, amplification reagents comprising primers 20, and detection probes 30 are added to vessel 40 to form a reaction mixture. After the addition of the reagents, the reaction mixture is subjected to amplification conditions so that a copy of the target strand 60 is produced as shown in FIG. 1(b). The mixture of FIG. 1(b) can then be heated to thermally disociate the double stranded amplicon as shown in FIG. 1 (c) which illustrates single stranded amplicon members 70. The mixture of FIG. 1 (c) is then cooled and probes 80 bind the single stranded amplicon members 70 to form probe/single stranded amplicon member complexes shown in FIG. 1 (d). FIG. 1 (e) illustrates a method of detecting the complexes. As shown by FIG. 1 (e), the complexes are immobilized to solid phase reagent 90, and conjugate 100 is immobilized to the complexes. The presence of the complexes on the solid phase reagent can then be detected as an indication of the presence of the target sequence in the test sample. FIG. 2 shows a diagram of the reaction complex wherein the large open circle represents a solid phase, Y_Y represents a probe sequence to which a hapten (Y) is attached at both ends, anti-Y represents an anti-hapten Y antibody, X represents a different hapten, anti-X represents an antibody against hapten X, and (*) represents a detectable signal generating compound. It should be noted that the probe and the primer each can be attached to a different hapten such as adamantane and carbazole, and attachment can occur at either the 5' end, the 3' end, both the 5' and 3' ends; or, more than one hapten can be attached at or near the 5' or the 3' end. In the following examples, SEQUENCE ID NOs 1, 2, 6, 7, 16, 18, 19, 21, 22, 25, 26 and 27 had adamantane attached at position 1 of each's 5' end unless otherwise noted; SEQUENCE ID NOs 3, 4, 5, 8, 9, 10, 11, 12, 13, 14, 15, 30 and 31 had carbazole attached at the final nucleotide position at each's 3' end unless otherwise noted; and SEQUENCE ID NOs 17, 20, 23, 24, 28 and 29 each had carbazole attached at position 1 of the 5' end and the final nucleotide position of the 3' end, unless otherwise noted.

The primers and probes disclosed herein are useful in typical PCR assays, wherein the test sample is contacted with a pair of primers, amplification is performed, the hybrdization probe is added, and detection is performed.

The present invention will now be described by way of examples, which are meant to illustrate, but not to limit, the spirit and scope of the invention.

EXAMPLES

Example 1

Amplification with HGBV NTR Primer Set

Target-specific primer detection probes were designed to detect the above target sequence by oligonucleotide hybridization PCR. These primers were SEQUENCE ID NO 1 and SEQUENCE ID NO 2.

A. NTR Primer Set. Target sequences were amplified using the NTR primer set (SEQUENCE ID NO 1 and SEQUENCE ID NO 2) and haptenated with adamantane at their 5' end using standard cyanoethyl phosphoramidite coupling chemistry.

The amplified product then was detected using different hybridization probes as shown in TABLE 1. Specificity was assessed using human placental DNA (hp DNA; Sigma, St. Louis, Mo.). Reactivity was assessed by using plasmid DNA containing NTR sequence.

TABLE 1

| Reaction | Target | Primer | Detection Probe |
|---|---|---|---|
| 1 | 1 µg hpDNA | NTR S1/NTR A1 (SEQ ID NO 1/ SEQ ID NO 2) | NTR CJ1 (SEQ ID NO 3) |

TABLE 1-continued

| Reaction | Target | Primer | Detection Probe |
|---|---|---|---|
| 2 | 2 ng NTR Plasmid | NTR S1/NTR A1 (SEQ ID NO 1/ SEQ ID NO 2) | NTR CJ1 (SEQ ID NO 3) |
| 3 | 4 ng NTR Plasmid | NTR S1/NTR A1 (SEQ ID NO 1/ SEQ ID NO 2) | NTR CJ1 (SEQ ID NO 3) |
| 4 | 1 µg hpDNA | NTR S1/NTR A1 (SEQ ID NO 1/ SEQ ID NO 2) | NTR CJ2 (SEQ ID NO 4) |
| 5 | 2 ng NTR Plasmid | NTR S1/NTR A1 (SEQ ID NO 1/ SEQ ID NO 2) | NTR CJ2 (SEQ ID NO 4) |
| 6 | 4 ng NTR Plasmid | NTR S1/NTR A1 (SEQ ID NO 1/ SEQ ID NO 2) | NTR CJ2 (SEQ ID NO 4) |
| 7 | 1 µg hpDNA | NTR S1/NTR A1 (SEQ ID NO 1/ SEQ ID NO 2) | NTR RM1 (SEQ ID NO 5) |
| 8 | 2 ng NTR Plasmid | NTR S1/NTR A1 (SEQ ID NO 1/ SEQ ID NO 2) | NTR RM1 (SEQ ID NO 5) |
| 9 | 4 ng NTR Plasmid | NTR S1/NTR A1 (SEQ ID NO 1/ SEQ ID NO 2) | NTR RM1 (SEQ ID NO 5) |
| 10 | 1 µg hpDNA | NTR S1/NTR A1 (SEQ ID NO 1/ SEQ ID NO 2) | NTR CJ1/CJ2/RM1 (SEQ ID NO 3/ SEQ ID NO 4/ SEQ ID NO 5) |
| 11 | 2 ng NTR Plasmid | NTR S1/NTR A1 (SEQ ID NO 1/ SEQ ID NO 2) | NTR CJ1/CJ2/RM1 (SEQ ID NO 3/ SEQ ID NO 4/ SEQ ID NO 5) |
| 12 | 4 ng NTR Plasmid | NTR S1/NTR A1 (SEQ ID NO 1/ SEQ ID NO 2) | NTR CJ1/CJ2/RM1 (SEQ ID NO 3/ SEQ ID NO 4/ SEQ ID NO 5) |

*The NTR plasmid (Clone pHGBV-C clone #1) was deposited at the American Type Culture Collection, 12301 Parklawn Drive, Rockville, Maryland 20852 as of November 8, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. pHGBV-C clone #1 was accorded A.T.C.C. Deposit No. 69711. The HGBV cDNA sequences in all of the deposited materials are incorporated herein by reference.

B. Description of plasmid. PCR extension was performed for reactions 1–12 (see Table 1) as described below using the 10× PCR buffer (Perkin Elmer, Foster City, Calif.) which consisted of 100 mM Tris-HCl, pH 8.3, 500 mM KCl. The MgCl2 final concentration was 2 mM and the final concentration of the nucleotides was @200 µM. The reaction conditions for Table 1 are shown in Table 2.

TABLE 2

| Reactions | Primer Concentration | Probe Concentration | Enzyme Concentration |
|---|---|---|---|
| 1–12 | 0.25 µM | 0.01 µM | 10 U Taq |

*Reactions were amplified as follows: 95° C. 2' 1 cycle; 94° C. 1'/55° C. 1'/72° C. 1' 30 cycles; 95° C. 5', 15° C. soak Following amplification, reaction products were detected on the Abbott LCx® system (available from Abbott Laboratories, Abbott Park, Ill.). The data from these experiments are presented in TABLE 3. The data in TABLE 3 demonstrated specific amplification and detection of the HGBV target sequence.

TABLE 3

| Reaction* | LCx ® (c/s/s) | Reactivity |
|---|---|---|
| 1 | 14.7 | Nonreactive |
| 2 | 725.5 | Reactive |
| 3 | 776.2 | Reactive |
| 4 | 12.4 | Nonreactive |
| 5 | 703.8 | Reactive |
| 6 | 772.4 | Reactive |
| 7 | 12.0 | Nonreactive |
| 8 | 339.9 | Reactive |
| 9 | 360.4 | Reactive |
| 10 | 12.8 | Nonreactive |
| 11 | 954.5 | Reactive |
| 12 | 962.4 | Reactive |

*Reactions correspond to those in Table 1.

Example 2

Amplification with NS3 Primer Set

A. NS3 Primer Set. The target sequence was amplified using the NS3 primer set (NS3 S1 and NS3 A1, SEQUENCE ID NOS 7 and 6, respectively) and haptenated with adamantane at their 5' end as described in Example 1. The amplified product was detected using different hybridization probes as shown in TABLE 3 and haptenated with carbazole at their 3' end using standard cyanoethyl coupling chemistry. Nonspecific amplification/hybridization was assessed using human placental DNA (hpDNA; Sigma, St. Louis, M.) or ribosomal RNA (rRNA; Boehringer Mannheim, Indianapolis, Ind.). Reactivity was assessed using plamid containing NS3 sequence.

TABLE 4

| Reaction | Target | Primer | Detection Probe |
|---|---|---|---|
| 1 | 250 ng hpDNA | NS3 A1 + NS3 S1 (SEQ ID NO 7 + SEQ ID NO 6) | NS3 CJ1 + NS3 CJ2 (SEQ ID NO 8 + SEQ ID NO 9) |
| 2 | 10 fg NS3 plasmid | NS3 A1 + NS3 S1 (SEQ ID NO 7 + SEQ ID NO 6) | NS3 CJ1 + NS3 CJ2 (SEQ ID NO 8 + SEQ ID NO 9) |
| 3 | 1 pg NS3 plasmid | NS3 A1 + NS3 S1 (SEQ ID NO 7 + SEQ ID NO 6) | NS3 CJ1 + NS3 CJ2 (SEQ ID NO 8 + SEQ ID NO 9) |
| 4 | 30 pg NS3 plasmid | NS3 A1 + NS3 S1 (SEQ ID NO 7 + SEQ ID NO 6) | NS3 CJ1 + NS3 CJ2 (SEQ ID NO 8 + SEQ ID NO 9) |
| 5 | 500 ng rRNA | NS3 A1 + NS3 S1 (SEQ ID NO 7 + SEQ ID NO 6) | NS3 RM5 + NS3 RM6 (SEQ ID NO 14 + SEQ ID NO 15) |
| 6 | $2.7 \times 10^6$ NS3 RNA molecules | NS3 A1 + NS3 S1 (SEQ ID NO 7 + SEQ ID NO 6) | NS3 RM5 + NS3 RM6 (SEQ ID NO 14 + SEQ ID NO 15) |
| 7 | 500 ng rRNA | NS3 A1 + NS3 S1 (SEQ ID NO 7 + SEQ ID NO 6) | NS3 RM1 + NS3 RM4 (SEQ ID NO 10 + SEQ ID NO 13) |
| 8 | 10 fg NS3 plasmid | NS3 A1 + NS3 S1 (SEQ ID NO 7 + SEQ ID NO 6) | NS3 RM1 + NS3 RM4 (SEQ ID NO 10 + SEQ ID NO 13) |
| 9 | 100 fg NS3 plasmid | NS3 A1 + NS3 S1 (SEQ ID NO 7 + SEQ ID NO 6) | NS3 RM1 + NS3 RM4 (SEQ ID NO 10 + SEQ ID NO 13) |
| 10 | 500 ng rRNA | NS3 A1 + NS3 S1 (SEQ ID NO 7 + SEQ ID NO 6) | NS3 RM2 + NS3 RM4 (SEQ ID NO 11 + SEQ ID NO 13) |
| 11 | 10 fg NS3 plasmid | NS3 A1 + NS3 S1 (SEQ ID NO 7 + SEQ ID NO 6) | NS3 RM2 + NS3 RM4 (SEQ ID NO 11 + SEQ ID NO 13) |
| 12 | 100 fg NS3 plasmid | NS3 A1 + NS3 S1 (SEQ ID NO 7 + SEQ ID NO 6) | NS3 RM2 + NS3 RM4 (SEQ ID NO 11 + SEQ ID NO 13) |
| 13 | 500 ng rRNA | NS3 A1 + NS3 S1 (SEQ ID NO 7 + SEQ ID NO 6) | NS3 RM3 + NS3 RM4 (SEQ ID NO 12 + SEQ ID NO 13) |
| 14 | 10 fg NS3 pasmid | NS3 A1 + NS3 S1 (SEQ ID NO 7 + SEQ ID NO 6) | NS3 RM3 + NS3 RM4 (SEQ ID NO 12 + SEQ ID NO 13) |
| 15 | 100 fg NS3 plasmid | NS3 A1 + NS3 S1 (SEQ ID NO 7 + SEQ ID NO 6) | NS3 RM3 + NS3 RM4 (SEQ ID NO 12 + SEQ ID NO 13) |

B. Description of the NS3 plasmid. PCR extension was performed using 5× EZ buffer (Perkin Elmer, Foster City Calif.) which consisted of 250 mM Bicine, 575 mM postasium acetate, 40% (w/v) glycerol, pH 8.2, and Mn(OAc)2 at 2.5 mM final concentration. The nucleotides were at a concentration of 200 μM. The reaction conditions for TABLE 6 are shown in TABLE 5 below.

The NS3 plasmid (Clone pHGBV-C clone #1) was deposited at the American Type Culture Collection, 12301 Parklawn Drive, Rockville, Md as of Nov. 8, 1994, under the terms of the Budapest Treaty and will be maintained for a period of thirty (30) years from the date of deposit, or for five (5) years after the last request for the deposit, or for the enforceable period of the U.S. patent, whichever is longer. The deposits and any other deposited material described herein are provided for convenience only, and are not required to practice the present invention in view of the teachings provided herein. pHGBV-C clone #1 was accorded A.T.C.C. Deposit No. 69711. The HGBV cDNA sequences in all of the deposited materials are incorporated herein by reference.

TABLE 5

| Reactions | Primer Concentration | Probe Concentration | Enzyme Concentration |
|---|---|---|---|
| 1–4* | 0.25 μM | 0.01 μM | 5 U rTth |
| 5,6** | 0.25 μM | .01 μM | 5 U rTth |
| 7–15*** | 0.25 μM | .005 μM | 5 U rTth |

*Cycling/hybridization conditions: 95° C. 2' 1 cycle; 94° C. 1'/55° C. 1'/72° C. 1' 30 cycles; 95° C. 5', 15° C. soak;
**Cycling/hybridization conditions: 55° C. 30', 94° C. 2' 1 cycle; 94° C. 1', 55° C. 1', 72° C. 1' 35 cycles; 97° C. 5', 15° C. soak;
***Cycling/hybridization Conditions: 94° C., 2' 1 cycle; 94° C. 1', 55° C. 1', 72° C. 1' 35 cycles; 97°, 5', 15° soak Following amplification, reaction products were hybridized and detected on the Abbott LCx® system. These data are presented in TABLE 6. The data in TABLE 4 demonstrated specific amplification and detection of the HGBV target sequence.

TABLE 6

| Reaction* | LCx ® (c/s/s) |
|---|---|
| 1 | 33.2 |
| 2 | 1269.9 |
| 3 | 1888.3 |
| 4 | 1944.3 |
| 5 | 15.5 |
| 6 | 245.4 |
| 7 | 11.6 |
| 8 | 68.0 |

TABLE 6-continued

| Reaction* | LCx ® (c/s/s) |
|---|---|
| 9 | 155.7 |
| 10 | 13.3 |
| 11 | 141.5 |
| 12 | 203.6 |
| 13 | 15.8 |
| 14 | 80.6 |
| 15 | 133.4 |

*Reactions correspond to those in Table 4.

Example 3

GB Serum Sample PCR/LCx° Parameters

"IVDU 300" was a sample known to contain the GB agent. It was tested as described hereinbelow. The negative control was normal serum.

A. HGBV 5' NTR Detection.

The target sequences (TABLE 7) were PCR amplified using the primers (SEQ ID No. 1 and 2) and detection probes (SEQ ID No. 3 and 4) as described in Example 1. For this study, the primers were at a concentration of 0.25 mM ($3.0 \times 10^{13}$ molecules) and the detection probes were at a concentration of 0.01 mM ($1.2 \times 10^{12}$ molecules). In addition there was 0.025 units/ml (5 units total) of rTth DNA polymerase and 20 ng total of rRNA.

The reverse transcriptase reaction was performed for 60° C. for 30 minutes. The product was PCR amplified under the following cycling conditions: 94° C. for 1 min./55° C. for 1 min./72° C. for 1 min for 40 cycles. Next, the oligomer hybridization step was a 95° C., 5', 15° C. soak.

Following amplification, reaction products were detected on the Abbott LCx® system (available from Abbott Laboratories, Abbott Park, Ill.). The data from these experiments are presented in TABLE 7. The data in TABLE 7 demonstrated specific amplification and detection of the HGBV target sequence.

TABLE 7

| sample | prep method | serum equivalents, ml | LCx ® avg. c/s/s |
|---|---|---|---|
| control | QIAgen* | 0.25 | 24 |
| control | RNAzol B** | 2.5 | 26 |
| IVDU 300 | QIAgen | 0.25 | 251 |
| IVDU 300 | RNAzol B | 2.5 | 432 |

*QIAgen nucleic acid purification method obtained from QIAgen, Inc. (CA)
**RNAzol B nucleic acid purification method from Biotecx (Houston, TX)

B. HGBV NS3 Detection

Reactivity of RNA samples (TABLE 8) were PCR amplified using the primers (SEQ ID No. 6 and 7) and detection probes (SEQ ID No. 14 and 15) as described in Example 2. For this study, the primers were at a concentration of 0.25 mM ($3.0 \times 10^{13}$ molecules) and the detection probes were at a concentration of 0.01 mM ($1.2 \times 10^{12}$ molecules.). In addition there was 0.025 units/ml (5 units total) of rTth DNA polymerase and 500 ng total of rRNA as assay control.

The reverse transcriptase reaction was performed at 64° C. for 10 minutes/62° C. for 10 minutes/60° C. for 10 min./58° C. for 10 min./56° C. for 10 min./54° C. for 10 min./52° C. for 10 min./50° C. for 10 min. The product was PCR amplified under the following cycling conditions: 94° C. for 1 min./55° C. for 1.5 min. for 40 cycles. Next, the oligomer hybridization step was a 95° C., 5', 15° C. soak.

Following amplification, reaction products were detected on the Abbott LCx® system (available from Abbott Laboratories, Abbott Park, Ill.). The data from these experiments are presented in TABLE 8. The data in TABLE 8 demonstrated specific amplification and detection of the HGBV target sequence.

TABLE 8

| Sample | Prep method | serum equivalents, ml | LCx ® avg. c/s/s |
|---|---|---|---|
| control | QIAgen* | 0.25 | 38 |
| control | RNAzol B** | 2.5 | 31 |
| IVDU 300 | QIAgen | 0.25 | 148 |
| IVDU 300 | RNAzol B | 2.5 | 373 |

*QIAgen nucleic acid purification method obtained from QIAgen, Inc. (CA)
**RNAzol B nucleic acid purification method from Biotecx (Houston, TX)

Example 4

Amplification with HGBV NTR Primer Set

Target-specific primer detection probes were designed to detect the above target sequence by oligonucleotide hybridization PCR. These primers utilized were SEQUENCE ID NO 1 and SEQUENCE ID NO 16.

A. NTR Primer Set. Target sequences were amplified using the NTR primer set (SEQUENCE ID NO 1 and SEQUENCE ID NO 16) and haptenated with adamantane at their 5' end using standard cyanoethyl phosphoramidite coupling chemistry.

The amplified product then was detected using probe 3FS3 (SEQUENCE ID NO 17) on the Abbott LCx® system. The probe had been haptenated with carbazole at its 3' end using standard cyanoethyl coupling chemistry. The results are presented below in TABLE 9.

TABLE 9

| REACTION No.* | LCx ® (c/s/s) | REACTIVITY |
|---|---|---|
| 1 | 19 | $H_2O$ |
| 2 | 23.5 | rRNA |
| 3 | 39 | Nonreactive Sample |
| 4 | 1635.0 | Reactive Sample |

*Cycling conditions were as follows: 94° C., 1', 60° C., 30'; 94° C., 1', 64° C., 1'30' for 40 cycles; 97° C., 5', 15° C., 2' to soak.

B. Futher Studies. Target sequences were amplified using additional NTR primer sets and haptenated with adamantane at their 5' end using standard cyanoethyl phosphoramidite coupling chemistry. The amplified product then was detected using various probes identified below in TABLE 10 on the Abbott LCx system. The probes had been haptenated with carbazole at their 3' end using standard cyanoethyl coupling chemistry.

TABLE 10

| Primer | Detection Probe | Reaction | LCx ® (c/s/s) | Reactivity |
|---|---|---|---|---|
| SEQ ID NO 18/ SEQ ID NO 19 | SEQ ID NO 4/ SEQ ID NO 20 | 1 | 17.8; 24.2; 22.9; 17.4 | $H_2O$ |
| | | 2 | 20.3; 21.1; 22.3; 21.5 | rRNA, 500 ng |
| | | 3 | 21.0; 20.6 | NR*, 1:10 |
| | | 4 | 23.4; 21.9 | NR, 1:50 |
| | | 5 | 1099.1; | R‡, 1:10 |

TABLE 10-continued

| Primer | Detection Probe | Reaction | LCx ® (c/s/s) | Reactivity |
|---|---|---|---|---|
| | | | 1047.7 | |
| | | 6 | 945.5; 748.8 | R, 1:50 |
| | | 7 | 938.7; 760.1 | R, 1:10 |
| | | 8 | 355.5; 696.1 | R, 1:50 |
| SEQ ID NO 21/ SEQ ID NO 22 | SEQ ID NO 23 | 1 | 31.6, 32.0 | H₂O |
| | | 2 | 33.4; 34.6 | Poly A |
| | | 3 | 1158.2; 1173.6 | Transcript, 5e2 molecules |
| | | 4 | 47.3; 50.7 | NR, 1:40 |
| | | 5 | 37.5; 38.7 | NR, 1:400 |
| | | 6 | 1110.9; 1105.7 | R, 1:40 |
| | | 7 | 792.8; 546.7 | R, 1:400 |

•NR = Nonreactive;
‡R = Reactive

Example 5

Performance Studies of Various Primer Combinations with Same Probe

Various combinations of primer combinations were tested as described in Example 3 hereinabove with the same probe, in order to assess the sensitivity and specificity of these various combinations. The various combinations tested are presented in TABLE 11, below, and are coded as combination "A," "B," "C," and "D." Results of these combinations, letter coded as "A," "B," "C," and "D" are shown below in TABLE 12. Note that for probes SEQUENCE ID NO 3, the probe is attached to carbazole at both the 5' end at position 1 and the 3' end at position 15.

TABLE 11

| Primer Combinations | | |
|---|---|---|
| Probe | Primers | Combination |
| SEQ ID NO 3 + SEQ ID NO 20 + SEQ ID NO 24 | SEQ ID NO 1 + SEQ ID NO 2 | A |
| SEQ ID NO 3 + SEQ ID NO 20 + SEQ ID NO 24 | SEQ ID NO 25 + SEQ ID NO 2 | B |
| SEQ ID NO 3 + SEQ ID NO 20 + SEQ ID NO 24 | SEQ ID NO 1 + SEQ ID NO 26 | C |
| SEQ ID NO 3 + SEQ ID NO 20 + SEQ ID NO 24 | SEQ ID NO 25 + SEQ ID NO 26 | D |

TABLE 12

| Reactivity of Combinations | | | |
|---|---|---|---|
| Combination | Reaction | LCx ® (c/s/s) | Reactivity |
| A (366 bp amplicon) | 1 | 22.1, 22.9 | HCV plasmid DNA, 1 pg |
| | 2 | 1568.9, 1609.9 | ntr plasmid DNA, 100 fg |
| | 3 | 1637.2, 1583.6 | ntr plasmid DNA, 1 pg |
| B (297 bp amplicon) | 1 | 28.3, 30.0 | HCV plasmid DNA, 1 pg |
| | 2 | 1738.5, 1590.1 | ntr plasmid DNA, 100 fg |
| | 3 | 1744.3, 1744.9 | ntr plasmid DNA, 1 pg |
| C (446 bp amplicon)* | 1 | 18.7, 18.0 | HCV plasmid DNA, 1 pg |

TABLE 12-continued

| Reactivity of Combinations | | | |
|---|---|---|---|
| Combination | Reaction | LCx ® (c/s/s) | Reactivity |
| | 2 | 1092.9, 1174.5 | ntr plasmid DNA, 100 fg |
| | 3 | 1343.6, 1284.8 | ntr plasmid DNA, 1 pg |
| D (367 bp amplicon)* | 1 | 30.1, 27.8 | HCV plasmid DNA, 1 pg |
| | 2 | 669.6, 680.8 | ntr plasmid DNA, 100 fg |
| | 3 | 1198.6, 1236.8 | ntr plasmid DNA, 1 pg |

*note that for combinations C and D, 69° C. annealing temperature was used to accomodate the high GC content of the primer SEQUENCE ID NO 26.

Example 6

Sensitivity and Specificity of Primer and Probe Combination Dependent

Various combinations of primer combinations were tested as described in Example 6 hereinabove with the same probe, in order to assess the sensitivity and specificity of these various combinations. The various combinations tested are presented in TABLE 13, below, and are coded as combination "A," "B," "C," "D," and "E." Results of these combinations, letter coded as "A," "B," "C," "D," and "E" are shown below in TABLE 14.

TABLE 13

| PRIMER | PROBE | COMBINATION |
|---|---|---|
| SEQ ID NO 1 + SEQ ID NO 2 | SEQ ID NO 3• + SEQ ID NO 20 | A |
| SEQ ID NO 1 + SEQ ID NO 2 | SEQ ID NO 17 | B |
| SEQ ID NO 1 + SEQ ID NO 16 | SEQ ID NO 17 | C |
| SEQ ID NO 25 + SEQ ID NO 19 | SEQ ID NO 3• AND SEQ ID NO 20 | D |
| SEQ ID NO 27 + SEQ ID NO 16 | SEQ ID NO 17 | E¤ |

•SEQ ID NO 3 had Carbazole attached at the 5' end at position 1 and the 3' end at position 15.
¤60° C. was used to adjust the lower annealing temperature of the mismatched sense primer SEQUENCE ID NO 27.

TABLE 14

| Combination | Reaction | LCx ® (c/s/s) | Reactivity |
|---|---|---|---|
| A (366 bp amplicon) | 1 | 355.9, 269.5 | Transcript°, e3 molecules |
| | 2 | 36.7, 38.5 | NR• (JS)¤1:10 |
| | 3 | 76.7, 107.4 | R‡, (HS) 1:10 |
| | 4 | 197.4, 205.4 | R, (XT) 1:10 |
| | 5 | 36.7, 38.5 | NR, (JS) 1:10 |
| B (366 bp amplicon) | 1 | 140.5, 164.9 | Transcript, e3 molecules |
| | 2 | 54.5, 43.6 | NR, (JS) 1:10 |
| | 3 | 84.2, 93.0 | R, (HS) 1:10 |
| | 4 | 198.6, 243.7 | R, (XT) 1:10 |
| | 5 | 37.0, 31.4 | NR, (JS) 1:10 |
| C (119 bp amplicon) | 1 | 1743.4, 1783.3 | Transcript, e3 molecules |
| | 2 | 40.1, 101.1 | NR, (JS) 1:10 |
| | 3 | 2072.8, 2057.4 | R, (HS) 1:10 |
| | 4 | 2197.0, 2116.9 | R, (XT) 1:10 |
| | 5 | 32.4, 32.7 | NR (JS), 1:10 |

TABLE 14-continued

| Combination | Reaction | LCx ® (c/s/s) | Reactivity |
|---|---|---|---|
| D (235 bp amplicon) | 1 | 191.4, 228.2 | Transcript, e3 molecules |
| | 2 | 41.9, 39.9 | NR, (JS) 1:10 |
| | 3 | 176.2, 167.1 | R, (HS) 1:10 |
| | 4 | 1370.4, 1415.2 | R, (XT) 1:10 |
| | 5 | 35.5, 40.5 | NR, (JS), 1:10 |
| | 1 | 1573.3, 1672.6 | Transcript, e3 molecules |
| | 2 | 57.3, 100.7 | NR, (JS) 1:10 |
| | 3 | 1174.2, 1009.9 | R, (HS) 1:10 |
| | 4 | 2178.0, 2148.1 | R, (XT) 1:10 |
| | 5 | 39.3, 40.0 | NR, (JS) 1:10 |

*NR = nonreactive;
‡R = reactive;
¤( ) the letters in the parenthesis indicate the identifying code of the patient sample;
°Transcript containing NTR or NS3 specific sequence at $10^3$ molecules.

Example 6

Use of Nongenerative Primers to Detect GBV-C NS3

A primer pair (SEQUENCE ID NO 18 and SEQUENCE ID NO 19) was tested following the procedures as described in Example 3 hereinabove with the probe SEQUENCE ID NO 28 and SEQUENCE ID NO 29, in order to determine the performance of the primer pair and probe. The cycling conditions were 94° C., 1', 55° C., 20'; 94° C., 1', 51° C., 1'30' for 40 cycles; 97° C., 5', 15° C., 2' to soak. The PCR cycling conditions were faster and less complicated than touchdown PCR. K. H. Roux, *Bio Techniques* 16:812–814 (1994). The results of the reaction are set forth in TABLE 15, below.

TABLE 15

| REACTION | LCx ® (c/s/s) | SAMPLE |
|---|---|---|
| 1 | 56.6 | rRNA, 500 ng |
| 2 | 40.4 | rRNA, 500 ng |
| 3 | 234.1 | RNA Transcript*, e6 |
| 4 | 216.4 | RNA Transcript, e6 |
| 5 | 799.2 | RNA Transcript, e7 |
| 6 | 781.3 | RNA Transcript, e7 |
| 7 | 1090.7 | RNA Transcript, e8 |
| 8 | 1048.6 | RNA Transcript, e8 |

*Transcript containing NTR or NS3 specific sequence at $10^{6,7 \, \alpha \, 8}$ molecules The probes of the present invention described herein thus are useful for detecting HGBV in individuals. Other uses or variations of the present invention will be apparent to those of ordinary skill of the art when considering this disclosure. Therefore, the present invention is intended to be limited only by the appended claims.

We claim:

1. A probe specific for hepatitis GB virus 5' NTR selected from the group consisting of SEQUENCE ID NO 3, SEQUENCE ID NO 4 and SEQUENCE ID NO 5.

2. A probe specific for hepatitis GB virus 5' NTR selected from the group consisting of SEQUENCE ID NO 17, SEQUENCE ID NO 20 and SEQUENCE ID NO 23.

3. A composition comprising primer pair specific for hepatitis GB virus 5' NTR consisting of SEQUENCE ID NO 1 and SEQUENCE ID NO 2.

4. A composition comprising a primer pair specific for hepatitis GB virus 5' NTR consisting of SEQUENCE ID NO 1 and SEQUENCE ID NO 16.

5. A composition comprising a primer pair specific for hepatitis GB virus 5' NTR consisting of SEQUENCE ID NO 18 and SEQUENCE ID NO 19.

6. A composition comprising a primer pair specific for hepatitis GB virus 5' NTR consisting of SEQUENCE ID NO 21 and SEQUENCE ID NO 22.

7. A probe specific for hepatitis GB virus NS3 region selected from the group consisting of SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14 and SEQUENCE ID NO 15.

8. A composition comprising a primer pair specific for hepatitis GB virus NS3 region consisting of SEQUENCE ID NO 28 and SEQUENCE ID NO 29.

9. A composition comprising a primer pair specific for hepatitis GB virus NS3 region consisting of SEQUENCE ID NO 6 and SEQUENCE ID NO 7.

10. A composition comprising a primer pair specific for hepatitis GB virus NS3 region consisting of SEQUENCE ID NO 30 and SEQUENCE ID NO 31.

11. An assay for detecting the presence of HGBV target nucleotides in a test sample, comprising:
   a. contacting a test sample suspected of containing a target HGBV nucleotide sequence with an HGBV primer pair selected from the group consisting of the pair of SEQUENCE ID NO 1 and SEQUENCE ID NO 2, the pair of SEQUENCE ID NO 6 and SEQUENCE ID NO 7, the pair of SEQUENCE ID NO 1 and SEQUENCE ID NO 16, the pair of SEQUENCE ID NO 18 and SEQUENCE ID NO 19 and the pair of SEQUENCE ID NO 21 and SEQUENCE ID NO 22 to form a reaction mixture;
   b. contacting said reaction mixture with at least one HGBV probe selected from the group consisting of SEQUENCE ID NO 3, SEQUENCE ID NO 4, SEQUENCE ID NO 5, SEQUENCE ID NO 17, SEQUENCE ID NO 20, and SEQUENCE ID NO 23;
   c. detecting the presence of the HGBV target nucleotide in the test sample.

12. The assay of claim 11 where in said HGBV probe is conjugated to a detectable signal generating compound.

13. The assay of claim 12 wherein said signal generating compound is selected from the group consisting of a chemiluminescent compound, fluorescein and an enzyme.

14. The assay of claim 11 wherein said HGBV probe is conjugated to a hapten.

15. The assay of claim 14 wherein said hapten is selected from the group consisting of adamantane, carbazole, fluorescein and biotin.

16. An assay for detecting the presence of HGBV target nucleotides in a test sample, comprising:
   a. contacting a test sample suspected of containing a target HGBV nucleotide sequence with an HGBV primer pair selected from the group consisting of the pair of SEQUENCE ID NO 6 and SEQUENCE ID NO 7 and the pair of SEQUENCE ID NO 30 and SEQUENCE ID NO 31 to form a reaction mixture;
   b. contacting said reaction mixture with at least one HGBV probe selected from the group consisting of SEQUENCE ID NO 8, SEQUENCE ID NO 9, SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 28 and SEQUENCE ID NO 29;
   c. detecting the presence of the HGBV target nucleotide in the test sample.

17. The assay of claim 16 where in said HGBV probe is conjugated to a detectable signal generating compound.

18. The assay of claim 17 wherein said signal generating compound is selected from the group consisting of a chemiluminescent compound, fluorescein and an enzyme.

19. The assay of claim 16 wherein said HGBV probe is conjugated to a hapten.

20. The assay of claim 19 wherein said hapten is selected from the group consisting of adamantane, carbazole, fluorescein and biotin.

21. A test kit for detecting target HGBV nucleotide in a test sample, comprising:
   a. a container containing a primer pair specific for a HGBV target nucleotide, wherein said primer pair is selected from the group consisting of the pair of SEQUENCE ID NO 1 and SEQUENCE ID NO 2, the pair of SEQUENCE ID NO 6 and SEQUENCE ID NO 7, the pair of SEQUENCE ID NO 1 and SEQUENCE ID NO 16, the pair of SEQUENCE ID NO 18 and SEQUENCE ID NO 19 and the pair of SEQUENCE ID NO 21 and SEQUENCE ID NO 22;
   b. a container containing at least one probe specific for HGBV, wherein said probe is selected from the group consisting of SEQUENCE ID NO 3, SEQUENCE ID NO 4, SEQUENCE ID NO 5, SEQUENCE ID NO 17, SEQUENCE ID NO 20, and SEQUENCE ID NO 23.

22. The test kit of claim 21 wherein said HGBV probe is conjugated to a detectable signal generating compound.

23. The test kit of claim 22 wherein said signal generating compound is selected from the group consisting of a chemiluminescent compound, fluorescein and an enzyme.

24. The test kit of claim 21 wherein said HGBV probe is conjugated to a hapten.

25. The assay of claim 24 wherein said hapten is selected from the group consisting of adamantane, carbazole, fluorescein and biotin.

26. A test kit for detecting target HGBV nucleotide in a test sample, comprising:
   a. a container containing at least one primer pair specific for a HGBV target nucleotide wherein said primer pair is selected from the group consisting of the pair of SEQUENCE ID NO 6 and SEQUENCE ID NO 7, and the pair of SEQUENCE ID NO 30 and SEQUENCE ID NO 31;
   b. a container containing at least one probe specific for HGBV, wherein said probe is selected from the group consisting of SEQUENCE ID NO 8, SEQUENCE ID NO 9 and SEQUENCE ID NO 10, SEQUENCE ID NO 11, SEQUENCE ID NO 12, SEQUENCE ID NO 13, SEQUENCE ID NO 14, SEQUENCE ID NO 15, SEQUENCE ID NO 28 and SEQUENCE ID NO 29.

27. The test kit of claim 26 wherein said HGBV probe is conjugated to a detectable signal generating compound.

28. The test kit of claim 27 wherein said signal generating compound is selected from the group consisting of a chemiluminescent compound, fluorescein and an enzyme.

29. The test kit of claim 26 wherein said HGBV probe is conjugated to a hapten.

30. The assay of claim 29 wherein said hapten is selected from the group consisting of adamantane, carbazole, fluorescein and biotin.

* * * * *

UNITED STATES PATENT AND TRADEMARK OFFICE
CERTIFICATE OF CORRECTION

PATENT NO. : 5,709,997
DATED : Jan. 20, 1998
INVENTOR(S) : Marshall et al.

It is certified that error appears in the above-identified patent and that said Letters Patent is hereby corrected as shown below:

Column 42, line 16, change "and" to --,--.

Signed and Sealed this

Ninth Day of May, 2000

Attest:

Q. TODD DICKINSON

*Attesting Officer*    *Director of Patents and Trademarks*

SEQUENCE LISTING ( 1 ) GENERAL INFORMATION:

( i i i ) NUMBER OF SEQUENCES: 31

( 2 ) INFORMATION FOR SEQ ID NO:1:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:1:

CACTGGGTGC AAGCCCAGA A                                              2 1

( 2 ) INFORMATION FOR SEQ ID NO:2:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:2:

CACTGGTCCT TGTCAACTCG C                                              2 1

( 2 ) INFORMATION FOR SEQ ID NO:3:

( i ) SEQUENCE CHARACTERISTICS:
        ( A ) LENGTH: 15 base pairs
        ( B ) TYPE: nucleic acid (C) STRANDEDNESS: single
        (D) TOPOLOGY: linear (ii) MOLECULE TYPE: synthetic DNA (xi) SEQUENCE DESCRIPTION: SEQ ID NO:3:

AGGGTTGGTA GGTCG                                                                    15

(2) INFORMATION FOR SEQ ID NO:4:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:4:

CACGGTCCAC AGGTGTT                                                                  17

(2) INFORMATION FOR SEQ ID NO:5:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:5:

CGCAACGACGC CCATGTA                                                                 18

(2) INFORMATION FOR SEQ ID NO:6:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:6:

GGNRMKRTYC CYTTTTATGG GCATGG                                                        26

(2) INFORMATION FOR SEQ ID NO:7:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (ii) MOLECULE TYPE: synthetic DNA (xi) SEQUENCE DESCRIPTION: SEQ ID NO:7:

ACNACNAGGT CNCCRTCYTT GATGAT                                                        26

(2) INFORMATION FOR SEQ ID NO:8:

(i) SEQUENCE CHARACTERISTICS:
        (A) LENGTH: 14 base pairs
        (B) TYPE: nucleic acid
        (C) STRANDEDNESS: single
        (D) TOPOLOGY: linear (ii) MOLECULE TYPE: synthetic DNA ( x i ) SEQUENCE DESCRIPTION: SEQ ID NO:8:

AGGGGGGTCA AYGC　　　　　　　　　　　　　　　　　　　　　　　　　　14

( 2 ) INFORMATION FOR SEQ ID NO:9:

( i ) SEQUENCE CHARACTERISTICS:
        ( A ) LENGTH: 14 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:9:

GCYTATTAYV GGGG　　　　　　　　　　　　　　　　　　　　　　　　　　14

( 2 ) INFORMATION FOR SEQ ID NO:10:

( i ) SEQUENCE CHARACTERISTICS:
        ( A ) LENGTH: 15 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:10:

CAYTCNAAGG CGGAG　　　　　　　　　　　　　　　　　　　　　　　　　15

( 2 ) INFORMATION FOR SEQ ID NO:11:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:11:

YGYCAYTCNA AGGCGGAG　　　　　　　　　　　　　　　　　　　　　　　18

( 2 ) INFORMATION FOR SEQ ID NO:12:

( i ) SEQUENCE CHARACTERISTICS:
        ( A ) LENGTH: 21 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:12:

TTCYGYCAYT CNAAGGCGGA G　　　　　　　　　　　　　　　　　　　　21

( 2 ) INFORMATION FOR SEQ ID NO:13:

( i ) SEQUENCE CHARACTERISTICS:
        ( A ) LENGTH: 18 base pairs
        ( B ) TYPE: nucleic acid
        ( C ) STRANDEDNESS: single
        ( D ) TOPOLOGY: linear ( i i ) MOLECULE TYPE: synthetic DNA ( x i ) SEQUENCE DESCRIPTION: SEQ ID NO:13:

CATTCCTCTG GAGCGGAT　　　　　　　　　　　　　　　　　　　　　　　18

( 2 ) INFORMATION FOR SEQ ID NO:14:

( i ) SEQUENCE CHARACTERISTICS:
      ( A ) LENGTH: 16 base pairs
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:14:

GGGGGGTNAA YGCYAT                                                               16

( 2 ) INFORMATION FOR SEQ ID NO:15:

( i ) SEQUENCE CHARACTERISTICS:
      ( A ) LENGTH: 12 base pairs
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:15:

GCCTATTAYA GG                                                                   12

( 2 ) INFORMATION FOR SEQ ID NO:16:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:16:

ATTTACGACC TACCAACCCT G                                                         21

( 2 ) INFORMATION FOR SEQ ID NO:17:

( i ) SEQUENCE CHARACTERISTICS:
      ( A ) LENGTH: 15 base pairs
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:17:

AAAGGTGGTG GATGG                                                                15

( 2 ) INFORMATION FOR SEQ ID NO:18:

( i ) SEQUENCE CHARACTERISTICS:
      ( A ) LENGTH: 21 base pairs
      ( B ) TYPE: nucleic acid
      ( C ) STRANDEDNESS: single
      ( D ) TOPOLOGY: linear ( i i ) MOLECULE TYPE: synthetic DNA ( x i ) SEQUENCE DESCRIPTION: SEQ ID NO:18:

CAGGGTTGGT AGGTCGTAAA T                                                         21

( 2 ) INFORMATION FOR SEQ ID NO:19:

( i ) SEQUENCE CHARACTERISTICS:
      ( A ) LENGTH: 21 base pairs
      ( B ) TYPE: nucleic acid (C) STRANDEDNESS: single
(D) TOPOLOGY: linear (ii) MOLECULE TYPE: synthetic DNA (xi) SEQUENCE DESCRIPTION: SEQ ID NO:19:

CCGTACGTGG GCGTCGTTTG C                    21

(2) INFORMATION FOR SEQ ID NO:20:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:20:

TAGGTGGGTC TTAAG                           15

(2) INFORMATION FOR SEQ ID NO:21:

(i) SEQUENCE CHARACTERISTICS:
    (A) LENGTH: 21 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:21:

TCGCCCTTCA ATGTCTCTCT T                    21

(2) INFORMATION FOR SEQ ID NO:22:

(i) SEQUENCE CHARACTERISTICS:
    (A) LENGTH: 20 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:22:

CTGGGTGGCC CCATGCATTT                      20

(2) INFORMATION FOR SEQ ID NO:23:

(i) SEQUENCE CHARACTERISTICS:
    (A) LENGTH: 14 base pairs
    (B) TYPE: nucleic acid
    (C) STRANDEDNESS: single
    (D) TOPOLOGY: linear (ii) MOLECULE TYPE: synthetic DNA (xi) SEQUENCE DESCRIPTION: SEQ ID NO:23:

GGCGAGTTGA CAAG                            14

(2) INFORMATION FOR SEQ ID NO:24:

(i) SEQUENCE CHARACTERISTICS:
    (A) LENGTH: 15 base pairs
    (B) TYPE: nucleic acid
    (C) STRANDEDNESS: single
    (D) TOPOLOGY: linear (ii) MOLECULE TYPE: synthetic DNA ( x i ) SEQUENCE DESCRIPTION: SEQ ID NO:24:

ACGTCGCCCT TCAAT 15

( 2 ) INFORMATION FOR SEQ ID NO:25:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: synthetic DNA ( x i ) SEQUENCE DESCRIPTION: SEQ ID NO:25:

CGGCCAAAAG GTGGTGGATG G 21

( 2 ) INFORMATION FOR SEQ ID NO:26:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: synthetic DNA ( x i ) SEQUENCE DESCRIPTION: SEQ ID NO:26:

CGGAGCTGGG TGGCCCCATG C 21

( 2 ) INFORMATION FOR SEQ ID NO:27:

( i ) SEQUENCE CHARACTERISTICS:
  ( A ) LENGTH: 21 base pairs
  ( B ) TYPE: nucleic acid
  ( C ) STRANDEDNESS: single
  ( D ) TOPOLOGY: linear ( i i ) MOLECULE TYPE: synthetic DNA ( x i ) SEQUENCE DESCRIPTION: SEQ ID NO:27:

CACTAGGAGC AAGCCCCAGA A 21

( 2 ) INFORMATION FOR SEQ ID NO:28:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: synthetic DNA ( x i ) SEQUENCE DESCRIPTION: SEQ ID NO:28:

GGGGGGTNAA YGCYATTTGT TTGAACCGCA 30

( 2 ) INFORMATION FOR SEQ ID NO:29:

( i ) SEQUENCE CHARACTERISTICS:
  ( A ) LENGTH: 30 base pairs
  ( B ) TYPE: nucleic acid
  ( C ) STRANDEDNESS: single
  ( D ) TOPOLOGY: linear ( i i ) MOLECULE TYPE: synthetic DNA ( x i ) SEQUENCE DESCRIPTION: SEQ ID NO:29:

ATGCGGTTCA AACAAAGCCT ATTAYAGGGG 30

(2) INFORMATION FOR SEQ ID NO:30:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:30:

```
ATCCCCTTTT ATGGGCATGG                                      20
```

(2) INFORMATION FOR SEQ ID NO:31:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: synthetic DNA (xi) SEQUENCE DESCRIPTION: SEQ ID NO:31:

```
AGGTCTCCGT CCTTGATGAT                                      20
```